(12) United States Patent
Maglia et al.

(10) Patent No.: US 11,312,755 B2
(45) Date of Patent: Apr. 26, 2022

(54) BIOLOGICAL NANOPORES FOR BIOPOLYMER SENSING AND SEQUENCING BASED ON FRAC ACTINOPORIN

(71) Applicant: Rijksuniversiteit Groningen, Groningen (NL)

(72) Inventors: Giovanni Maglia, Glimmen (NL); Carsten Wloka, Hohen Neuendorf (DE); Natalie Lisa Mutter, Groningen (NL); Misha Soskine, Paris (FR); Gang Huang, Groningen (NL)

(73) Assignee: Rijksuniversiteit Groningen, Groningen (NL)

( * ) Notice: Subject to any disclaimer, the term of this patent is extended or adjusted under 35 U.S.C. 154(b) by 338 days.

(21) Appl. No.: 16/317,119

(22) PCT Filed: May 24, 2017

(86) PCT No.: PCT/NL2017/050331
§ 371 (c)(1),
(2) Date: Jan. 11, 2019

(87) PCT Pub. No.: WO2018/012963
PCT Pub. Date: Jan. 18, 2018

(65) Prior Publication Data
US 2019/0292235 A1 Sep. 26, 2019

Related U.S. Application Data

(60) Provisional application No. 62/360,999, filed on Jul. 12, 2016.

(51) Int. Cl.
*G01N 27/26* (2006.01)
*C07K 14/435* (2006.01)
(Continued)

(52) U.S. Cl.
CPC ...... *C07K 14/43595* (2013.01); *C12Q 1/6869* (2013.01); *G01N 27/44791* (2013.01);
(Continued)

(58) Field of Classification Search
CPC .. C12Q 1/6869; C12Q 1/68; G01N 27/44791; G01N 27/44756; G01N 27/447;
(Continued)

(56) References Cited

U.S. PATENT DOCUMENTS 6,362,002 B1* 3/2002 Denison ................ B82Y 15/00
435/6.12

FOREIGN PATENT DOCUMENTS

WO 2010/034018 A2 3/2010

OTHER PUBLICATIONS

Bellomio A et al: "Purification, cloning and characterization of fragaceatoxin C, a novel actinoporin from the sea anemone *Actinia fragacea*", TOXICON, Elmsford, NY, US, vol. 54, No. 6, Nov. 1, 2009 (Nov. 1, 2009), pp. 869-880, XP026499390, ISSN: 0041-0101, DOI: 10.1016/J.TOXICON.2009.06.022 [retrieved on Jun. 27, 2009].

(Continued)

*Primary Examiner* — Christine T Mui
(74) *Attorney, Agent, or Firm* — Banner & Witcoff, Ltd.

(57) ABSTRACT

The invention relates generally to the field of nanopores and the use thereof in various applications, such as analysis of biopolymers and macromolecules, typically by making electrical measurements during translocation through a nanopores. Provided is a system comprising a funnel-shaped proteinaceous nanopore comprising an a-helical pore-forming toxin that is a member from the actinoporin protein family, more in particular Fragaceatoxin C (FraC), a mutant FraC, a FraC paralog, or a FraC homolog.

12 Claims, 12 Drawing Sheets

Figure 1:
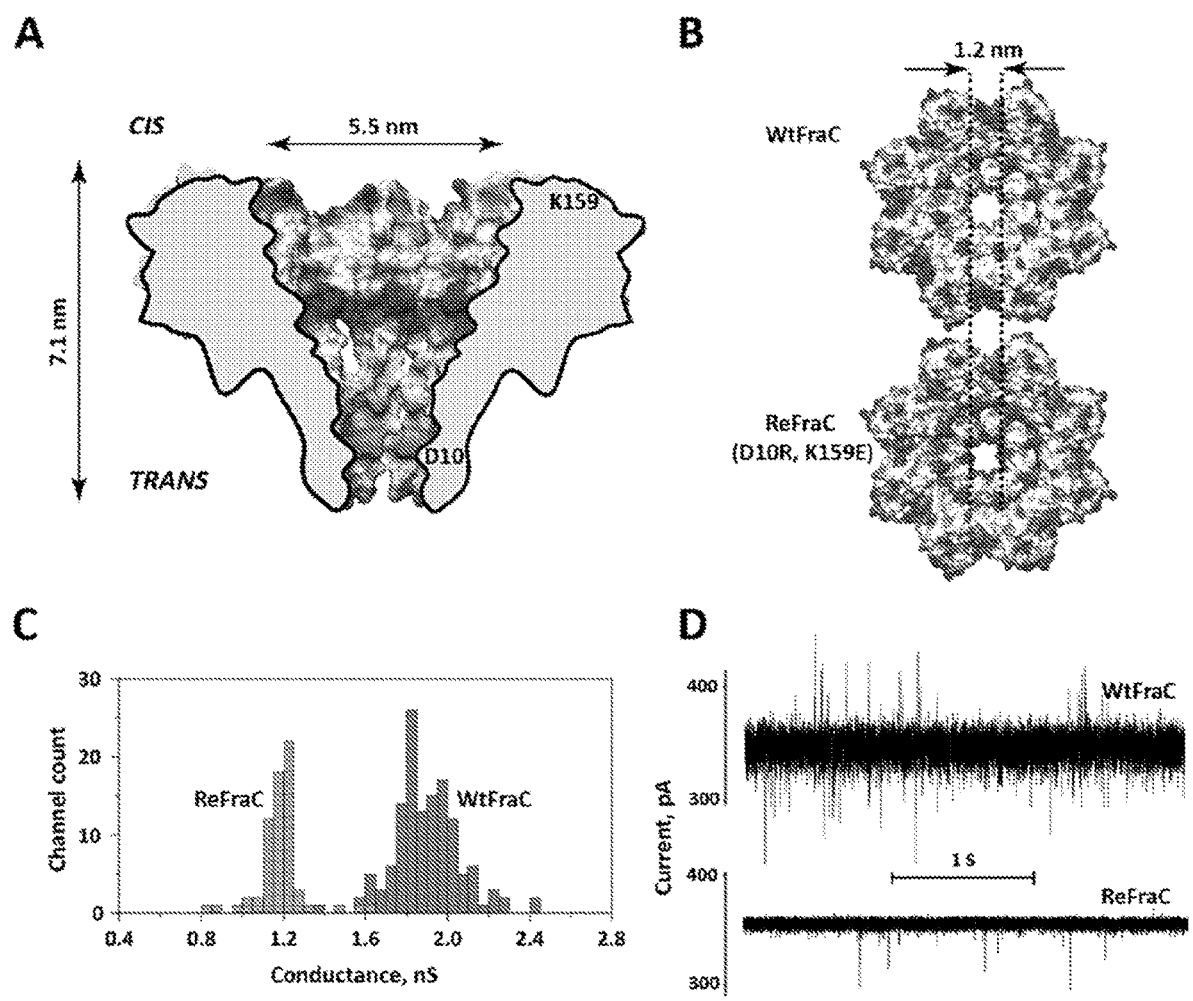

(51) Int. Cl.
  *C12Q 1/6869* (2018.01)
  *G01N 27/447* (2006.01)
  *G01N 33/487* (2006.01)
  *G01N 33/48* (2006.01)
  *C12Q 1/68* (2018.01)
  *B82Y 5/00* (2011.01)

(52) U.S. Cl.
  CPC .......... G01N 33/48721 (2013.01); *B82Y 5/00* (2013.01); *C07K 2319/00* (2013.01); *C07K 2319/03* (2013.01); *C07K 2319/21* (2013.01); *C07K 2319/22* (2013.01)

(58) Field of Classification Search
  CPC ................. G01N 27/403; G01N 27/26; G01N 33/48721; G01N 33/48707; G01N 33/487; G01N 33/483; G01N 33/48
  USPC .......................................................... 436/86
  See application file for complete search history.

(56) References Cited

OTHER PUBLICATIONS

Koldo Morante et al: "A Pore-Forming Toxin Requires a Specific Residue for Its Activity in Membranes with Particular Physicochemical Properties", Journal of Biological Chemistry, vol. 290, No. 17, Apr. 24, 2015 (Apr. 24, 2015), pp. 10850-10861, XP055401448, us ISSN: 0021-9258, DOI: 10.1074/jbc.M114.615211 see whole doc., esp. results.

Koji Tanaka et al: Structural basis for self-assembly of a cytolytic pore lined by protein and lipid:, Nature Communications, vol. 6, Feb. 26, 2015 (Feb. 26, 2015), p. 6337, XP055401446, DOI: 10.1038/ncomms7337 cited in the application see whole doc., esp. methods and p. 337, 2. col. 3. par.

* cited by examiner

BIOLOGICAL NANOPORES FOR BIOPOLYMER SENSING AND SEQUENCING BASED ON FRAC ACTINOPORIN

RELATED APPLICATIONS

This application is a National Stage Application under 35 U.S.C. 371 of co-pending PCT application PCT/NL2017/050331 designating the United States and filed May 24, 2017; which claims the benefit of US provisional application number 62/360,999 and filed Jul. 12, 2016 each of which are hereby incorporated by reference in their entireties.

The invention relates generally to the field of nanopores and the use thereof in various applications, such as analysis of biopolymers and macromolecules, typically by making electrical measurements during translocation through a nanopores.

Nanopores represent an attractive way to analyse biopolymers, for example to determine the identity of a polypeptide or polynucleotide, or to estimate the identity of individual building blocks in the polymer for sequencing purposes. This is because the method is label-free, provides measurements dependent on small numbers or even single molecules, and generates an electric signal that is highly scalable.

In a measurement system utilising a nanopore, some property of the system depends on the nucleotides in the nanopore, and electrical measurements of that property are taken. For example, a measurement system be created by placing a nanopore in an insulating membrane and measuring voltage-driven ion flow through the nanopore in the presence of nucleotides of the polynucleotide.

Nanopores have emerged as a powerful approach for single-molecule monitoring of chemical and enzymatic reactions, detection of proteins and sequencing of nucleic acids.[1],[2]. Phi29[3] as well as ClyA[4] have been shown to allow translocation of double stranded DNA. Recently, aerolysin was used to discriminate homopolymers consisting of adenine but differing in length.[5] To date, only αHL and MspA have been shown to discriminate nucleic acids. Both nanopores have ß-sheets in their transmembrane region. When DNA is threaded through MspA, the current blocked levels are affected by four or more nucleotides[6] while αHL has three sensing zones in its barrel-shape structure, which accommodates about 20 nucleobases.[7]

The present invention provides novel nanopores with different structures and recognition sites which offer improvements in sequencing accuracy and/or provide different error profiles. Here, we describe the purification and pre-oligomerization of Fragaceatoxin C (FraC), an α-helical pore-forming toxin that is a member from the actinoporin protein family, in complex with sphingomyelin and the reconstitution into planar lipid bilayers composed of 1,2-diphytanoyl-sn-glycero-3-phosphocholine (DPhPC). The present inventors furthermore engineered a FraC mutant (e.g. ReFraC) that permitted capture and translocation of ssDNA and discriminated homopolymers of adenine, thymine and cytosine immobilized with neutravidin (NA). Strikingly, dsDNA could be translocated through FraC, most probably via the elastically deformed α-helical constriction of the nanopore.

Notably, it was found that the FraC nanopore has an ideal shape for protein sequencing and folded protein analysis. It is shown herein below that the electro-osmotic flow is the dominant force that induces the entry of proteins and polypeptides inside the nanopore. By tuning the inner surface of the nanopore, either by precise engineering the constriction of the nanopore or by changing the solution pH, the translocation of both positively and negatively charged polypeptides could be observed. This is remarkable, because it shows that it is possible to induce an electro-osmotic flow that is strong enough to transport both positive and negative residues at a fixed applied potential. It was remarkably found that a series of (unfolded) proteins of different size, e.g. ranging from 1.2-25 kDa, can be distinguished on the basis of individual blockades. Using a 20 amino acid model polypeptide, it is demonstrated that even differences in a single amino acid residue can be observed by nanopore recordings, indicating that FraC nanopores allow the identification of specific sequence features in translocating polypeptides.

Furthermore, the inventors devised a method to reconstitute pre-oligomerized FraC nanopores in sphingomyelin-free planar lipid bilayers. The ReFraC nanopore was engineered to allow electrophoretic DNA capture and showed discrimination among ssDNA homopolymers. In contrast to other nanopores used to sequence DNA (e.g. αHL and MspA), FraC has a α-helical V-shaped transmembrane region which is advantageous to fine-tune nucleobase discrimination. This is because amino acids substitutions at different positions within the transmembrane α-helices may modulate both the size and chemical composition of the constriction.

It is also shown herein that ReFraC induces the unzipping of DNA duplexes at low applied potentials or allows their translocation at high applied potential. The unzipping of DNA hairpins or higher-ordered DNA structures has been investigated using the αHL nanopore.[20],[21] However, the cis vestibule of ReFraC (5.5 nm) is wider than that of αHL (2.6 nm)[13] or MspA (4.8 nm),[22] indicating that FraC can be advantageously employed to study larger higher-order dsDNA structures, such as G-quadruplexes, or folded RNA structures such as tRNAs.

Accordingly, in a first aspect the invention provides a system comprising a funnel-shaped proteinaceous nanopore comprising an α-helical pore-forming toxin that is a member from the actinoporin protein family. More specifically, the α-helical pore-forming toxin is Fragaceatoxin C (FraC), a mutant FraC, a FraC paralog, or a FraC homolog. FraC may be fused, preferably at its C-terminus, to a protein affinity tag, like a His-tag or Strep-tag.

Very good results can be obtained with a mutant FraC. For example, the mutant FraC comprises at least one substitution of a negatively charged amino acid residue in the narrow part of the pore into a neutral or positively charged amino acid residue, and/or at least one substitution of a neutral amino acid residue in the narrow part of the pore into a positively charged amino acid residue. For example, the mutant comprises at least one mutation in the transmembrane helices. Preferably, at least one negatively charged amino acid residue is changed into a positively charged amino acid residue. In a preferred embodiment, the mutant FraC comprises a mutation at position 10, preferably mutation Asp10Arg or Asp10Lys (residue numbering as in crystal structure PDB ID 4TSY). The mutant FraC may further comprise one or more compensatory mutation(s) to recover the hemolytic activity of FraC, preferably wherein said compensatory mutation is present at position 2, 9, 34, 52, 112, 150, 153 and/or 159, and/or preferably at position 159. For example, said compensatory mutation is selected from the group consisting of A2S, I9T, A34V, F52Y, W112L, T150I, G153D, K159E, I171T and any combination thereof. In a specific aspect the mutant FraC (further) comprises a mutation at position 159, preferably Lys159Glu. For example, the FraC double mutant D10R/K159E is used.

The nanopore may be is positioned between a first liquid medium and a second liquid medium, wherein at least one liquid medium comprises an analyte, and wherein the system is operative to detect a property of the analyte.

In one embodiment, the system is operative to translocate the analyte through the tunnel. In another embodiment, the system is operative to detect a property of the analyte comprises subjecting the nanopore to an electric field such that the analyte interacts with the nanopore. The applied potential (which creates the electric field) is necessary to have a current. The current is the output signal. For example, the system is operative to detect a property of the analyte comprises subjecting the nanopore to an electric field such that the analyte electrophoretically and/or electro-osmotically translocates through and/or is trapped in the nanopore. The property may be an electrical, chemical, or physical property of the analyte.

Preferably, the nanopore is comprised in a (planar) lipid bilayer. In a specific aspect, the lipid bilayer comprises or consists of phosphatidylcholine (PC), preferably 1,2-diphytanoyl-sn-glycero-3-phosphocholine.

In a second aspect, the invention provides a method for providing a system according to the invention, comprising the steps of providing recombinant monomers of said α-helical pore-forming toxin from the actinoporin protein family;

contacting said monomers with liposomes to assemble them into oligomers;

recovering the oligomers from the liposomes; and contacting the oligomers with a lipid bilayer, which may contain sphingomyelin, to allow the formation of nanopores.

In a third aspect, the invention provides a method comprising applying an electric field to a system as herein disclosed, wherein the funnel-shaped nanopore comprising an α-helical pore-forming toxin is positioned between a first conductive liquid medium and a second conductive liquid medium. At least one of the conductive liquid media may comprise an analyte. The method may further comprise the step of detecting the analyte in a method comprising measuring an ion current as the analyte interacts with the nanopore to provide a current pattern, wherein the appearance of a blockade in the current pattern indicates the presence of the analyte. The method may further comprise identifying the analyte, for example by comparing the current pattern to a known current pattern obtained using a known analyte under the same conditions. The analyte can be a nucleotide, a nucleic acid, an amino acid, a peptide, a protein, a polymer, a drug, an ion, a pollutant, a nanoscopic object, or a biological warfare agent.

In one embodiment, the analyte is a polymer, such as a protein, a peptide, or a nucleic acid. Preferably, the analyte is a nucleic acid, like ssDNA, dsDNA, RNA, or a combination thereof. In another preferred aspect, the analyte is a protein, a polypeptide or an oligopeptide, e.g. having a size of from about 1 to about 40 kDa, preferably about 1 to about 30 kDa. In one embodiment, the analyte is an oligopeptide (~10 or fewer amino acids), polypeptide (>10 amino acids) or folded protein (>50 amino acids).

In a method of the invention, the FraC nanopore is preferably a mutant FraC nanopore. The conductance through the tunnel of the mutant FraC nanopore is typically higher than the conductance through its corresponding wild-type FraC nanopore.

A still further aspect relates to a mutant Fragaceatoxin C (FraC) nanopore comprising at least a first mutant FraC monomer comprising at least one substitution of a negatively charged amino acid residue in the narrow part of the pore and/or at least one substitution of a neutral amino acid residue in the narrow part of the pore into a positively charged amino acid residue. For example, the mutant comprises at least one mutation in the transmembrane helices. Preferably, at least one negatively charged amino acid residue is changed into a positively charged amino acid residue. The mutant may comprise a substitution at position 3 or position 10, or both positions 3 and 10. In a preferred embodiment, the mutant FraC comprises a mutation at position 10, preferably mutation Asp10Arg or Asp10Lys (residue numbering as in crystal structure PDB ID 4TSY). The mutant FraC may further comprise one or more compensatory mutation(s) to recover the hemolytic activity of FraC, preferably wherein said compensatory mutation is present at position 2, 9, 34, 52, 112, 150, 153 and/or 159, and/or preferably at position 159. For example, said compensatory mutation is selected from the group consisting of A2S, I9T, A34V, F52Y, W112L, T150I, G153D, K159E, I171T and any combination thereof. In a specific aspect the mutant FraC (further) comprises a mutation at position 159, preferably Lys159Glu. Very good results can be obtained with the FraC double mutant D10R/K159E. Specifically preferred mutants include those of Table 3 herein below.

The mutant FraC nanopore may further comprise at least a second monomer selected from the group consisting of a wild-type FraC monomer, a second mutant FraC monomer, a wild-type FraC paralog or homolog monomer, and a mutant FraC paralog or homolog monomer, wherein the second mutant FraC monomer may be the same or different than the first mutant FraC monomer. For example, the second monomer is a wild-type FraC paralog or homolog monomer. In one embodiment, the first mutant FraC monomer of the mutant FraC nanopore comprises mutation D10R, preferably wherein the mutant is selected from those depicted in Table 3.

The mutant FraC nanopore preferably has a conductance through the tunnel that is higher than the conductance through the tunnel of its corresponding wild-type FraC nanopore.

The mutant FraC nanopore may further comprise a molecular motor, wherein the molecular motor is capable of moving an analyte into or through the nanopore with an average translocation velocity that is less than the average translocation velocity at which the analyte translocates into or through the nanopore in the absence of the molecular motor.

For example, the molecular motor is an enzyme, like a polymerase, an exonuclease, or a Klenow fragment.

For protein analysis, it is preferred to have an electroosmotic flow (EOF), from the cis to trans compartment, which is induced by a charged constriction. The translocation of amino acids of the same charge as the constriction can be obtained by manipulation of the pH of the analyte solution. It is advantageous to use one or more unnatural amino acids that maintain a negative charge at low pH values (<~4.5), for example sulfate ($SO_4^{2-}$), or phosphate ($PO_4^{2-}$) moieties are suitable amino acid side chain groups. Hence, also provided is a nanopore that is engineered to have a strong electroosmotic flow from the cis to trans compartment under negative applied potential (pH 4.5 or lower).

The invention also provides the use of a system as herein disclosed, or a mutant FraC nanopore according to the invention, for biopolymer sensing and/or biopolymer sequencing. For example, said biopolymer is a protein, a peptide, or a nucleic acid. Preferably, provided is the use of a system as herein disclosed, or a mutant FraC nanopore according to the invention, for sensing and/or sequencing of a nucleic acid, like ssDNA, dsDNA, RNA, or protein or polypeptide, or a combination thereof.

For example, a FraC nanopore is advantageously used to recognize protein, polypeptide and oligopeptide biomarkers. Once inside the nanopore proteins and polypeptides of different sizes can be distinguished by ionic currents. Although individual amino acids could not be identified on-the-fly during translocation, we showed that two small (unfolded) oligopeptides endothelin 1 and endothelin 2 (2,5 kDa), which differ by just one tryptophan residue could be differentiated by ionic current recordings. Therefore, if the translocation of a polypeptide can be controlled e.g. by the use of enzymes, FraC nanopores allow for the identification of specific sequence features in translocating polypeptides.

In one embodiment, a (mutant) FraC nanopore is used as a sensor in single-molecule proteomic analysis. In the simplest implementation of nanopore proteomics, proteins are recognized amino acid-by-amino acid as they translocate linearly through a nanopore. Since the sequence of proteins and oligopeptides in an organism is known from genomic analysis, proteins might be recognized simply by comparing a specific protein blockade during the unfolded translocation across a nanopore with a database of known protein blockades. Alternatively, folded proteins could be recognized as they lodge inside the nanopore vestibule with or without translocating the nanopore.

LEGEND TO THE FIGURES

FIG. 1. Wild type FraC (WtFraC) and D10R-K159E FraC (ReFraC) nanopores (A) Cross-section through octameric WtFraC showing coulombic surface coloring (red=negative charges, blue=positive charges). Aspartate residue 10, located in the constriction zone of WtFraC, is indicated. (B) Top view on WtFraC (top) and ReFraC (bottom). (C) Single channel conductance histogram for WtFraC (blue) and ReFraC (red) at +50 mV in 1M NaCl, 15 mM Tris.HCl pH 7.5. (D) Raw trace of WtFraC (top) and ReFraC (bottom) at +100 mV in 3 M NaCl, 15 mM Tris.HCl pH 7.5 buffer obtained with identical acquisition settings (2 kHz low-pass Bessel filter and 10 kHz sampling rate).

Figure 2:
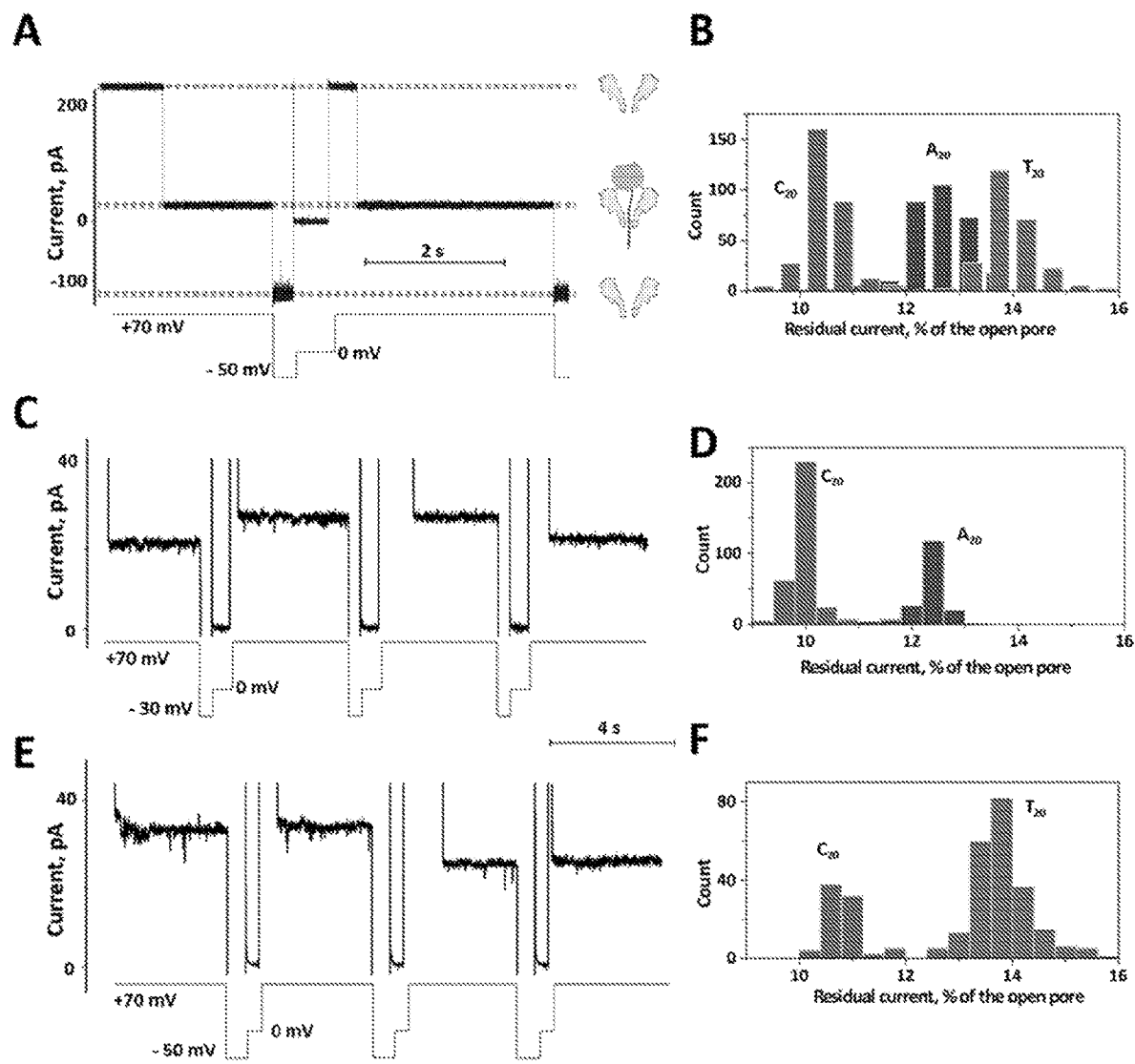

FIG. 2. DNA discrimination with ReFraC (A) Representative blockades of a homopolymeric DNA strand in complex with NA using ReFraC. The cartoon shows the interpretation of the current blockades. (B) Representative distributions of residual currents obtained for $A_{20}$, $C_{20}$, $T_{20}$ homopolymeric strands with ReFraC nanopores (C) Current blockades of a continuous trace induced by homopolymeric $C_{20}$ and $A_{20}$ nucleotides to the same ReFraC pore. Traces shown were digitally filtered with 100 Hz cut-off. (D) Distribution of residual currents imposed by mixtures of $C_{20}$ and $A_{20}$ homopolymeric strands (E) Continuous trace of an experiment to resolve mixtures of homopolymeric $C_{20}$ and $T_{20}$ nucleotides (F) Distribution of residual currents imposed by mixtures of $C_{20}$ and $T_{20}$ homopolymeric strands. Traces were recorded in 3 M NaCl, 15 mM Tris.HCl, pH 7.5, using 2 kHz low-pass Bessel filter and 10 kHz sampling rate. Traces C and E were subjected to additional 100 Hz Gaussian digital filtering.

Figure 3:
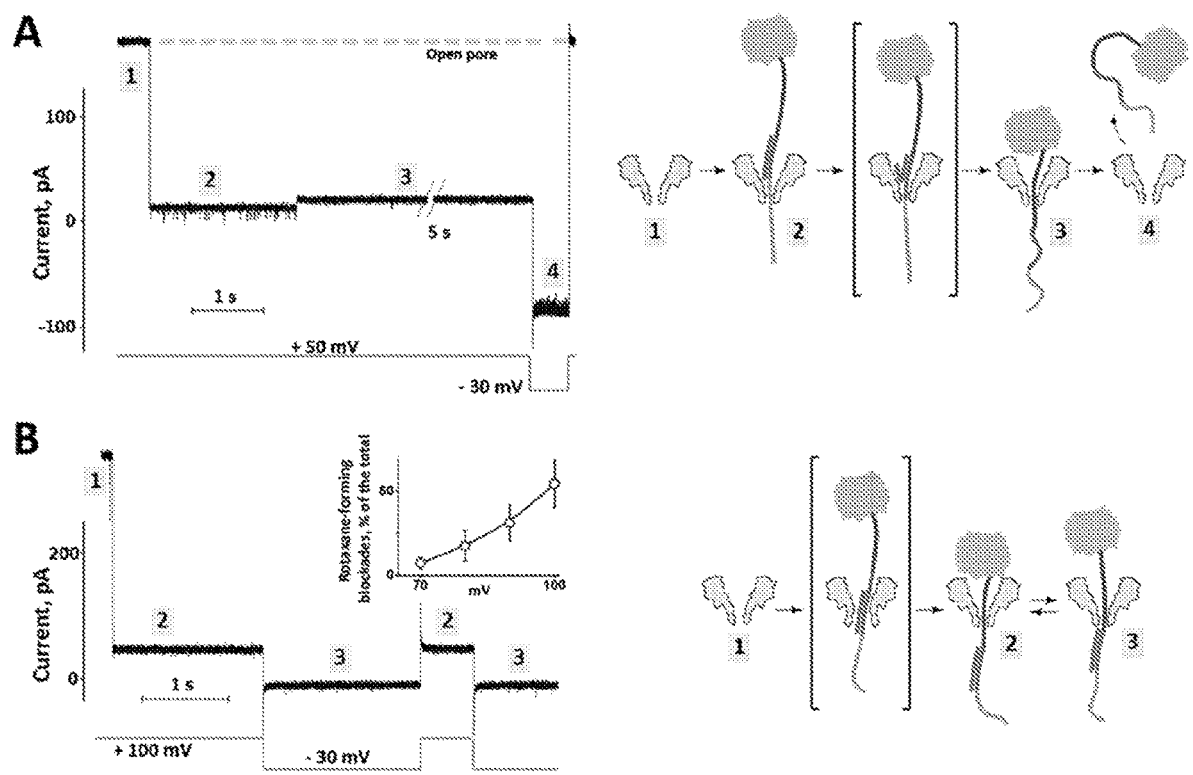

FIG. 3. Unzipping/Translocation of dsDNA by ReFraC (A) Representative trace of ReFraC capturing a NA:A (dsDNA)C complex at +50 mV. The open pore current is denoted as "1" and for comparison indicated after capture of the complex. Two levels can be observed in the block: firstly, a lower level ("2"), likely corresponding to homopolymeric cytosine which converts via an intermediate level (unzipping, brackets) into a higher level ("3"), most likely corresponding to homopolymeric adenine. Upon reversal of potential ("4") the block is immediately released indicating that the double-stranded region NA:A(dsDNA)C complex was peeled off. (B) At +100 mV, in more than half of the cases (insert) a single block ("2") is observed after the dsDNA part is pushed through (deformation, brackets) and upon application of −30 mV the block cannot be released immediately ("3"). At higher negative potentials the block can be released, indicating a rotaxane was formed (more examples in FIG. 8). Traces were recorded in 3 M NaCl, 15 mM Tris.HCl, pH 7.5, using 2 kHz low-pass Bessel filter and 10 kHz sampling rate.

Figure 4:
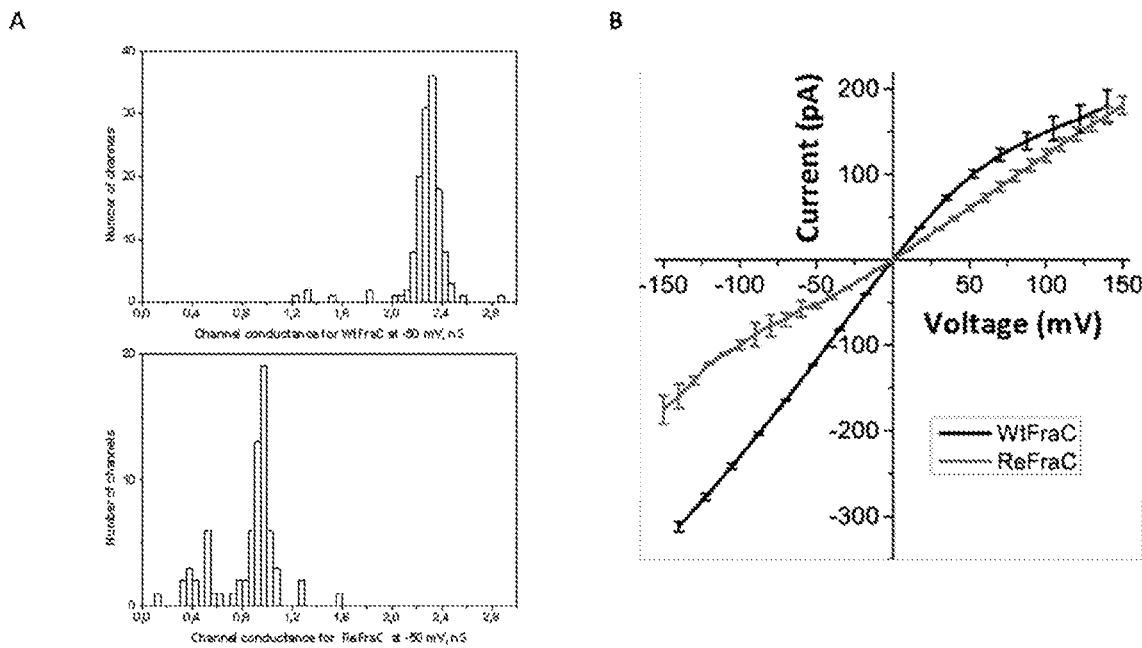

FIG. 4. Unitary channel conductance distribution and voltage current dependence determined for WtFraC and ReFraC nanopores. A: Unitary channel conductance distribution measured for WtFraC (top) and ReFraC (bottom) pre-oligomerized pores reconstituted in planar lipid bilayers. The conductance was measured at −50 mV applied potential. The orientation of each individual channel was verified according to the asymmetry in conductance. B: Voltage current dependence measured for WtFraC and ReFraC nanopores. Experiments were repeated 3 times, and error bars indicate the standard deviations between experimental values. Recordings were carried out in 15 mM Tris.HCl pH 7.5 and 1M NaCl.

Figure 5:
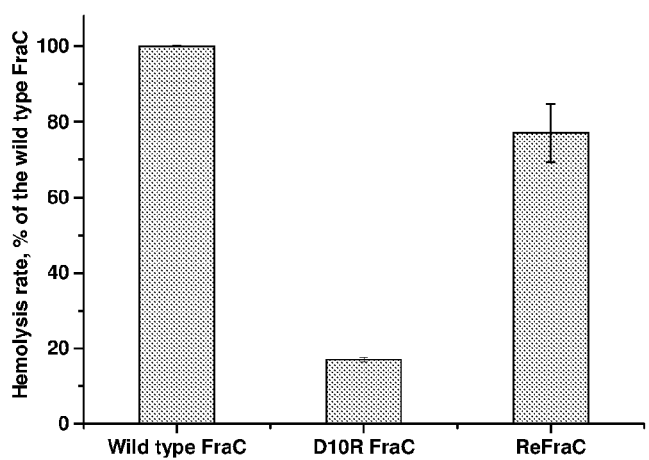

FIG. 5. Hemolytic activity of the WtFraC, D10R FraC and ReFraC. Hemolysis rate was calculated as inverse of the time elapsed till 50% decrease in turbidity (measured as optical density at 650 nm wavelength) observed in 1% of horse erythrocytes suspension in 15 mM Tris.HCl pH 7.5 150 mM NaCl. Proteins were added in 200 nM concentration, hemolysis rates are presented as percentage of WtFraC. Experiment was repeated 3 times, and error bars indicate the standard deviation between experimental values.

Figure 6:
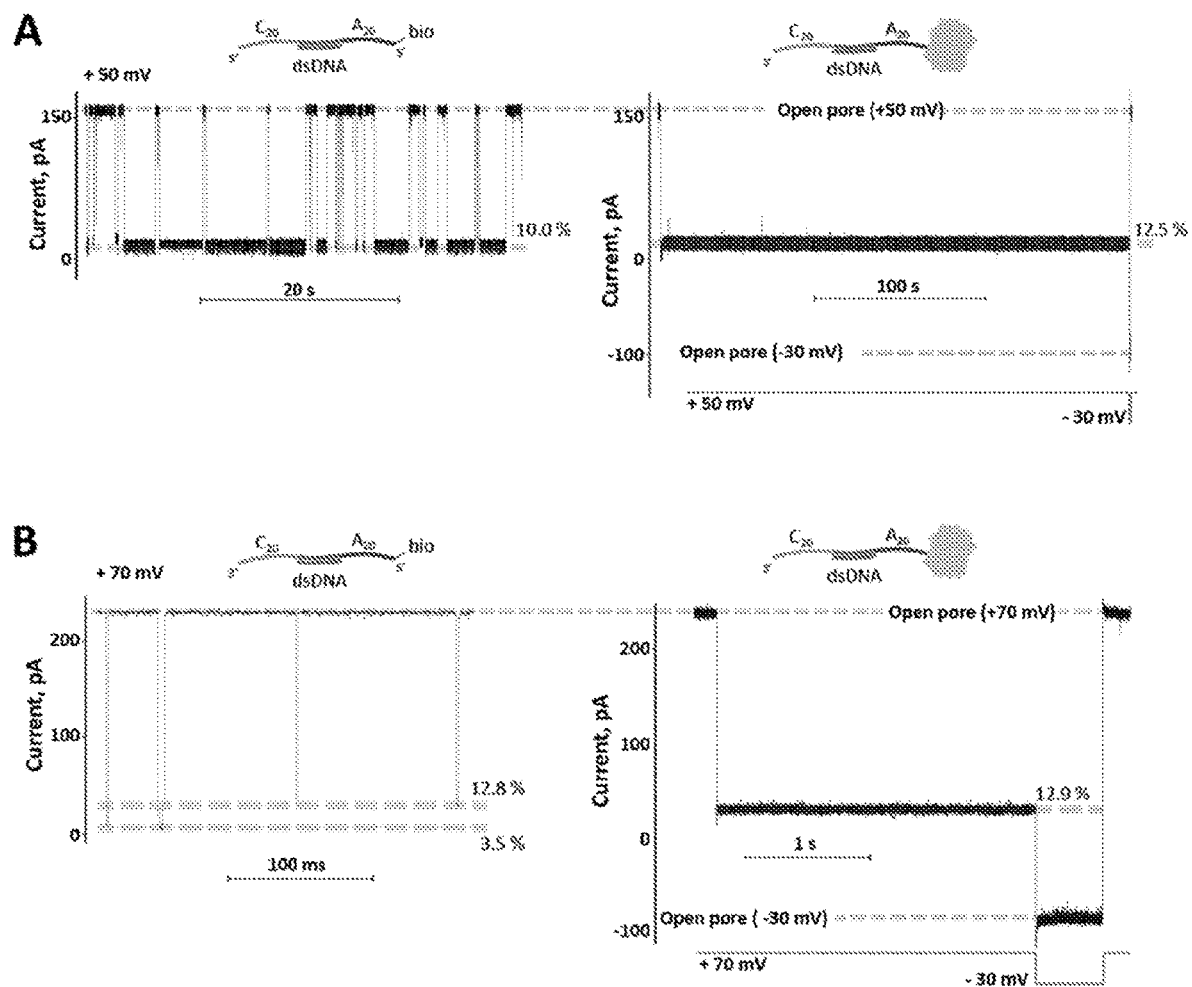

FIG. 6. Translocation and immobilization of A(dsDNA)C DNA substrate recorded with ReFraC nanopore. A(dsDNA)C substrate (depicted above the trace) was made by annealing of

```
oligo I
(5' biotinylated AAAAAAAAAAAAAAAAAAAAGTGCTACGAC
TCTCTGTGTGCCCCCCCCCCCCCCCCCCCC)
and oligo II
(CACACAGAGAGTCGTAGCAC).
```

A: Blockades provoked on ReFraC nanopore by 1 μM of A(dsDNA)C alone (left) and in complex with 0.25 μM of neutravidin (right), substrates were added in cis under +50 mV applied potential. B: Blockades provoked on ReFraC nanopore by 1 μM of A(dsDNA)C alone (left) and in complex with 0.25 μM of neutravidin (right), substrates were added in cis under at +70 mV. Two levels of the residual current detected for free A(dsDNA)C blockades indicated with pale violet dashed line. Current levels corresponding to the blocked and open pores are shown as pale violet and grey dashed lines respectively. Voltage stepping protocols are shown with the red lines below the traces. Recordings were carried out in 15 mM Tris.HCl pH 7.5 and 3M NaCl, sampling frequency was 10 kHz, and data were smoothed by 2 kHz low-pass Bessel filter upon acquisition.

Figure 7:
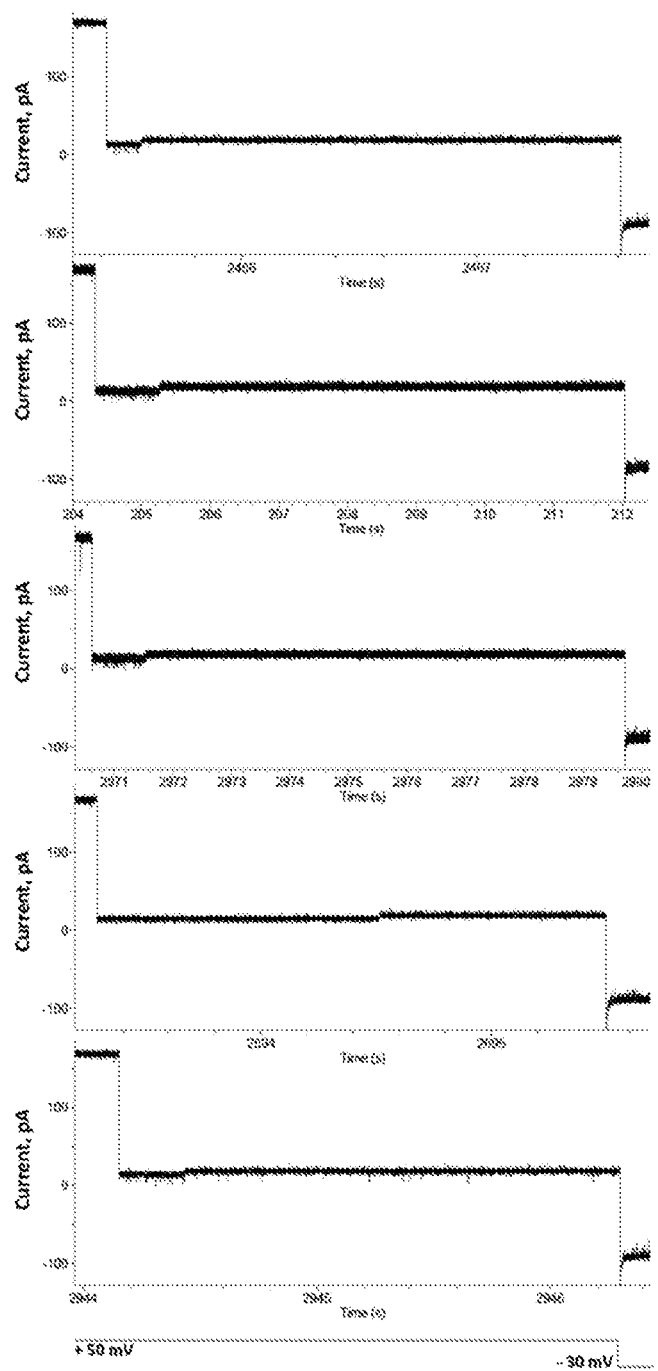

FIG. 7. Representative traces showing stepwise enhancements of the residual current within A(dsDNA)C-neutravidin blockades provoked on ReFraC nanopore. 1 μM of A(dsDNA)C and 0.25 µM of neutravidin were present in cis at +50 mV. Within the blockades residual current has switched from 8.8±0.7% (initial level) to 12.5±0.7% (final level). Voltage stepping protocol is shown with the red lines at the bottom. Recordings were carried out in 15 mM Tris.HCl pH 7.5 and 3M NaCl, sampling frequency was 10 kHz, and data were smoothed by 2 kHz low-pass Bessel filter upon acquisition.

Figure 8:
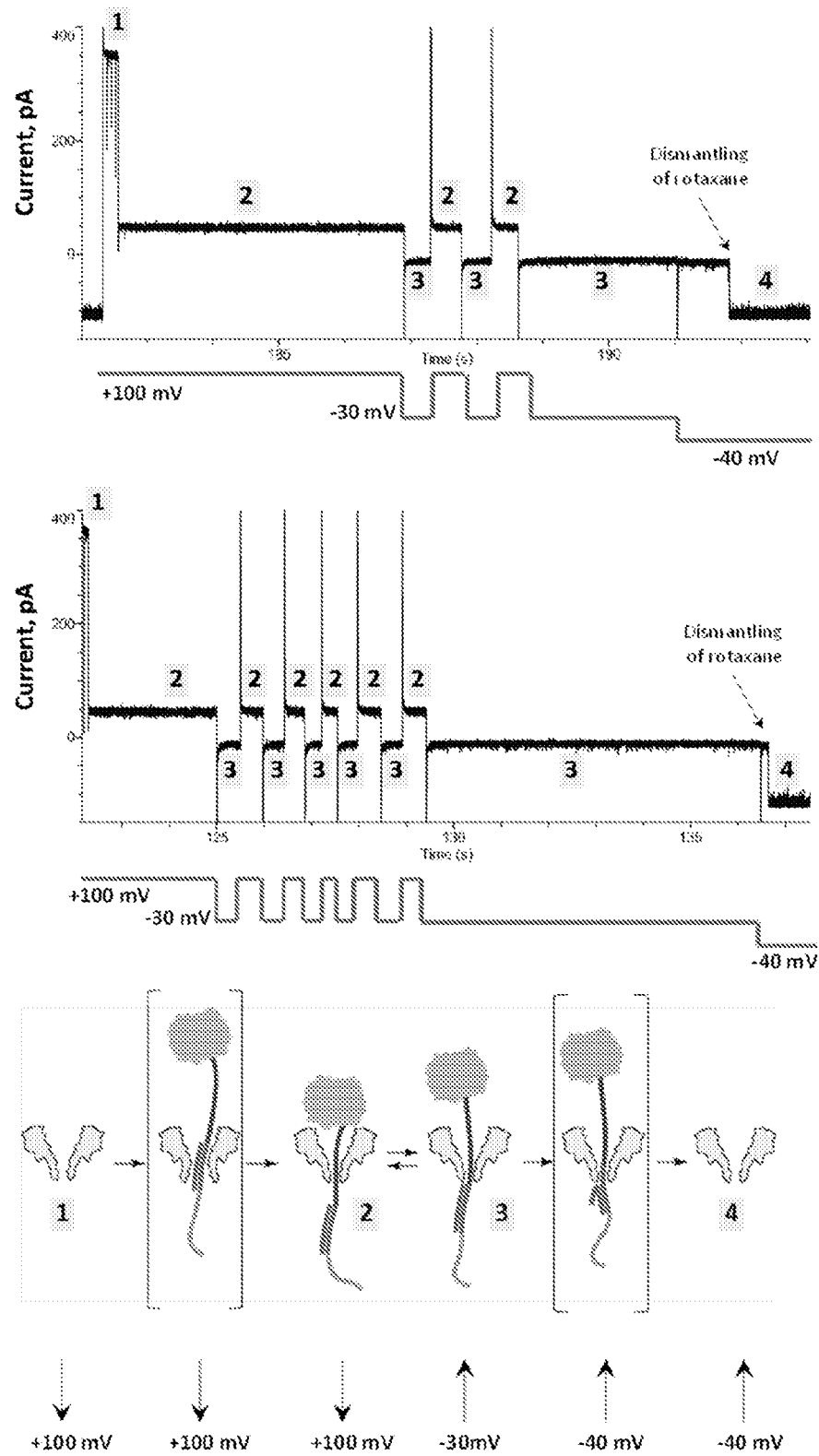

FIG. 8. Additional examples of traces showing rotaxane formation by A(dsDNA)C-neutravidin driven into ReFraC nanopore at +100 mV applied potential. 1 µM of A(dsDNA)C and 0.25 µM of neutravidin were added in cis. Voltage stepping protocols are shown with the red lines at the bottom. Rotaxanes were dismantled by switching the applied potential to –40 mV. Recordings were carried out in 15 mM Tris.HCl pH 7.5 and 3M NaCl, sampling frequency was 10 kHz, and data were smoothed by 2 kHz low-pass Bessel filter upon acquisition.

Figure 9:
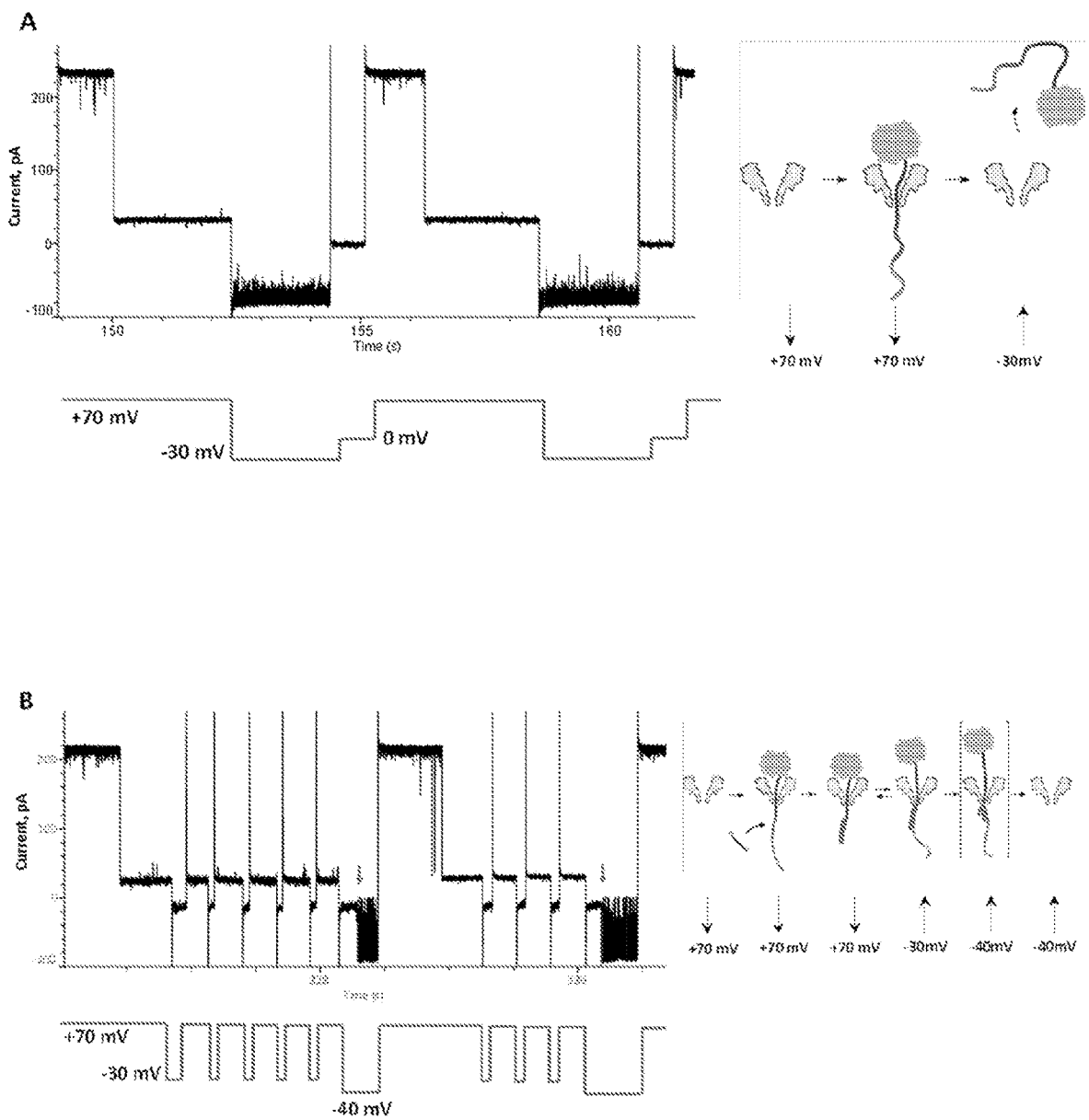

FIG. 9: Representative traces showing pseudorotaxane and rotaxane formation by oligonucleotide I—neutravidin immobilized within the ReFraC nanopore. A: Pseudorotaxane formation provoked by 1 µM of oligo I and 0.25 µM of neutravidin present in cis. B: Rotaxane formation by 1 µM of oligonucleotide I and 0.25 µM neutravidin present in cis while 1 µM of oligonucleotide II was added in trans. Rotaxanes were dismantled by switching the applied potential to –40 mV (red arrow above the trace indicates the dismantling of rotaxane). Transient state describing unzipping of dsDNA is shown in brackets. Voltage stepping protocol is shown with the red lines at the bottom. Recordings were carried out in 15 mM Tris.HCl pH 7.5 and 3M NaCl, sampling frequency was 10 kHz, and data were smoothed by 2 kHz low-pass Bessel filter upon acquisition.

Figure 10:
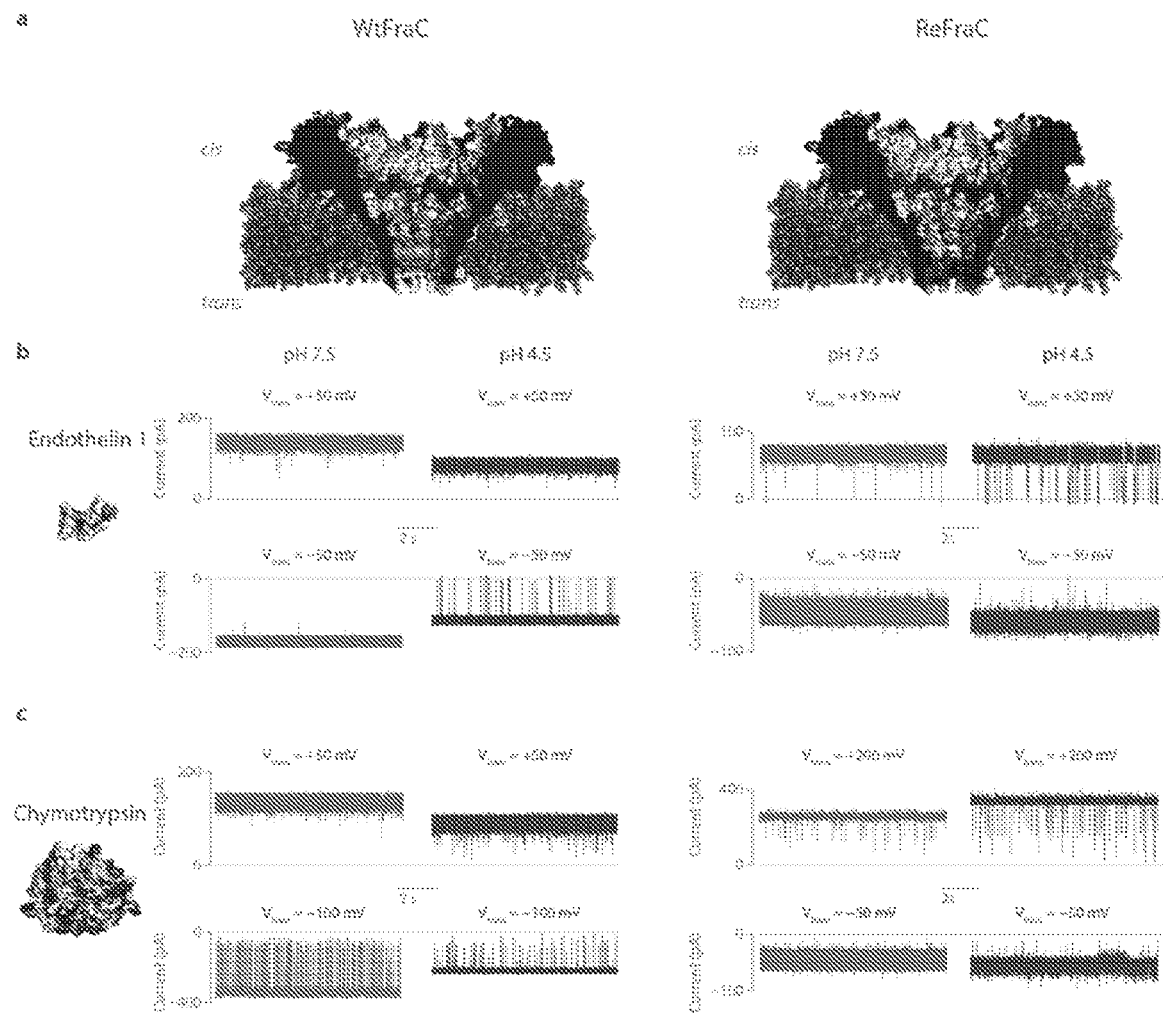

FIG. 10. Capture of an oligopeptide (Endothelin 1) and a protein (Chymotrypsin) with two FraC variants at two different pH conditions. a) Cross sections of wild type FraC (WtFraC, PDB: 4TSY) and D10R-K159E-FraC (ReFraC). b-c) Representative traces induced by 1 µM endothelin 1 (b) and 200 nM chymotrypsin (c) to WtFraC (left) and ReFraC (right). Chymotrypsin (PDB: 5CHA) and human endothelin 1 (PDB: 1EDN) are shown as surface representations. Endothelin 1 and chymotrypsin enter WtFraC under negative applied potentials, while they enter ReFraC under positive applied potentials. Chymotrypsin blockades to WtFraC were also observed under –50 mV at pH 7.5 and 4.5, however, the applied potential was increased to –100 mV to obtain a sufficient number of blockades. At pH 7.5, blockades to ReFraC by chymotrypsin under positive applied bias required higher potential than to WtFraC under negative applied bias. The buffer at pH 7.5 included 1 M KCl, 15 mM Tris, and the buffer at pH 4.5 contained 1 M KCl, 0.1 M citric acid, 180 mM Tris.Base. Endothelin 1 and chymotrypsin were added into cis compartment. All traces were recorded using 50 kHz sampling rate and a 10 kHz low-pass Bessel filter. The coloring represents the electrostatic potential of the molecular surface as calculated by APBS(13) (pH 7.5 in 1 M KCl) with red and blue corresponding to negative and positive potentials (range –4 to +4 kbT/ec), respectively. Structures were rendered using PyMOL.

Figure 11:
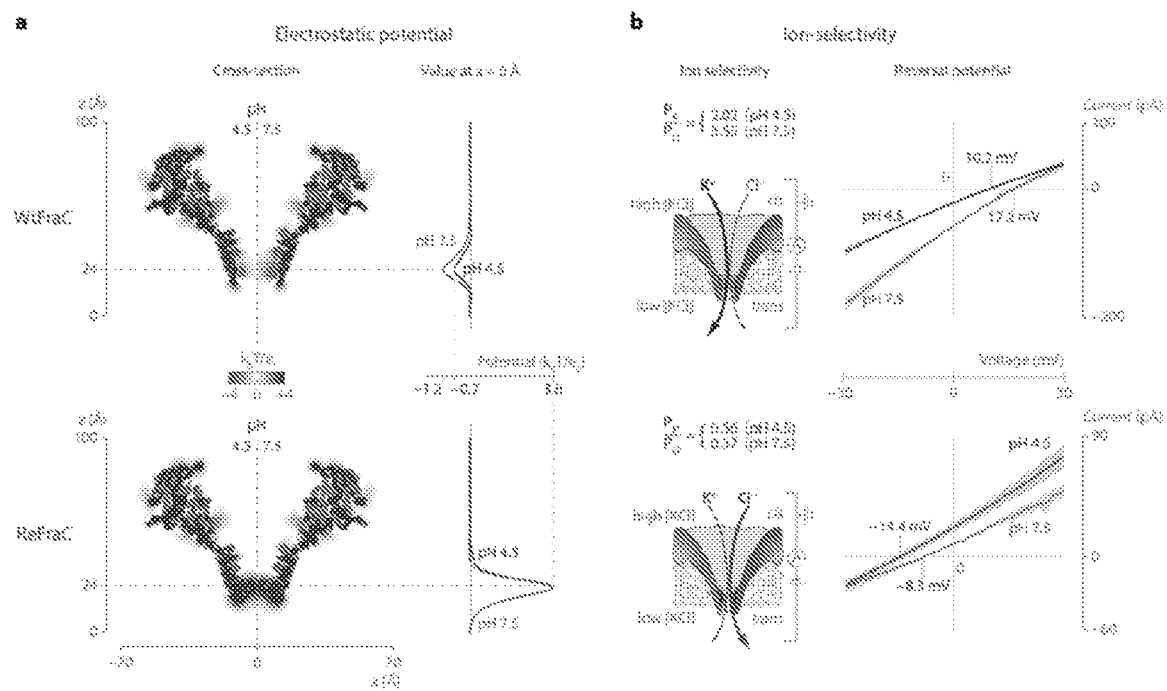

FIG. 11. Electrostatic distribution and ion-selectivity of WtFraC and ReFraC. a) The monomer averaged simulated electrostatic potentials reveal the negatively and positively charged constrictions of WtFraC and ReFrac, respectively. While for ReFrac lowering of the pH from 7.5 to 4.5 only had a small effect on the electrostatic potential, for WtFraC the peak value at the center of the constriction dropped ~41%. All simulations were performed using APBS(13) at 1M KCl, with the partial charge of each titratable residue adjusted according to their average protonation states with a modified version of the PDB2PQR software.(14) Residue pKa values were estimated using PROPKA.(33, 34) b) Determination of the reversal potential shows that WtFraC and ReFrac are respectively cation- and anion-selective, as expected from the electrostatic potentials at their constrictions. Lowering the pH from 7.5 to 4.5, reduced the ion selectivity of WtFraC ($P_{(K^+)}/P_{([Cl]^-)}$) by ~43%, in accordance with the reduced magnitude of the simulated electrostatic potential. By contrast, the ~37% increase in ion selectivity of ReFraC at pH 4.5 was not predicted by the simulations. All reversal potentials were measured under asymmetric salt conditions (467 mM KCl in trans and 1960 mM KCl in cis) and the ion selectivity determined using the Goldman-Hodgkin-Katz equation. Detailed experiment procedures are given in supporting information. The envelopes behind every current-voltage curve represent their respective standard deviations.

Figure 12:
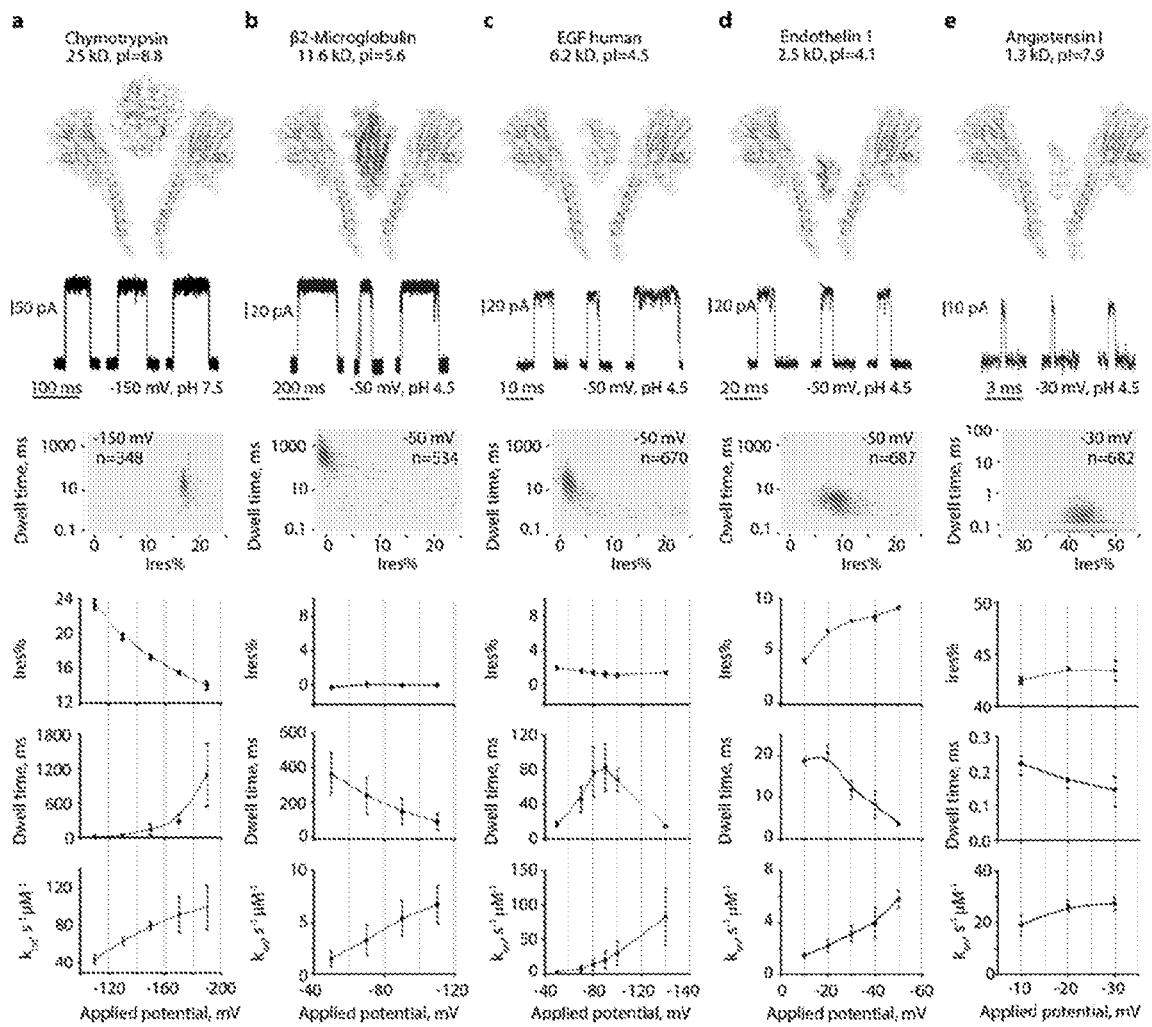

FIG. 12. Biomarker characterization with WtFraC at pH 4.5. a) From top to bottom: surface representation with molecular surface and cartoon representations (Pymol) of chymotrypsin (25 kD, PDB: 5CHA), a representative trace obtained under –150 mV applied potential, a heatplot depicting the dwell time distribution versus Ires % at –150 mV, the voltage dependence of Ires %, the voltage dependence of the dwell times, and the capture frequency. b), c), d), e) show the same information for ß2-microglobulin (11.6 kD, PDB: 1LDS), human EGF (6.2 kD, PDB: 1JL9), endothelin 1 (2.5 kD, PDB: 1EDN) and angiotensin I (1.3 kD), respectively. Angiotensin I is depicted as a random structure drawn with Pymol. The concentrations of the biomarkers were: 200 nM for chymotrypsin, 200 nM for ß2-microglobin, 2 µM for human EGF, 1 µM for endothelin 1, and 2 µM for angiotensin I, respectively. Isoelectric points of biomarkers are obtained from literatures or with the on line calculation tool Pepcalc. Error bars represent the standard deviation obtained from at least 3 repeats and at least 300 events for each repeat. Data were fitted using a B-spline function (Origin 8.1). All recordings were collected with 50 kHz sampling rate and 10 kHz low-pass Bessel filter.

Figure 13:
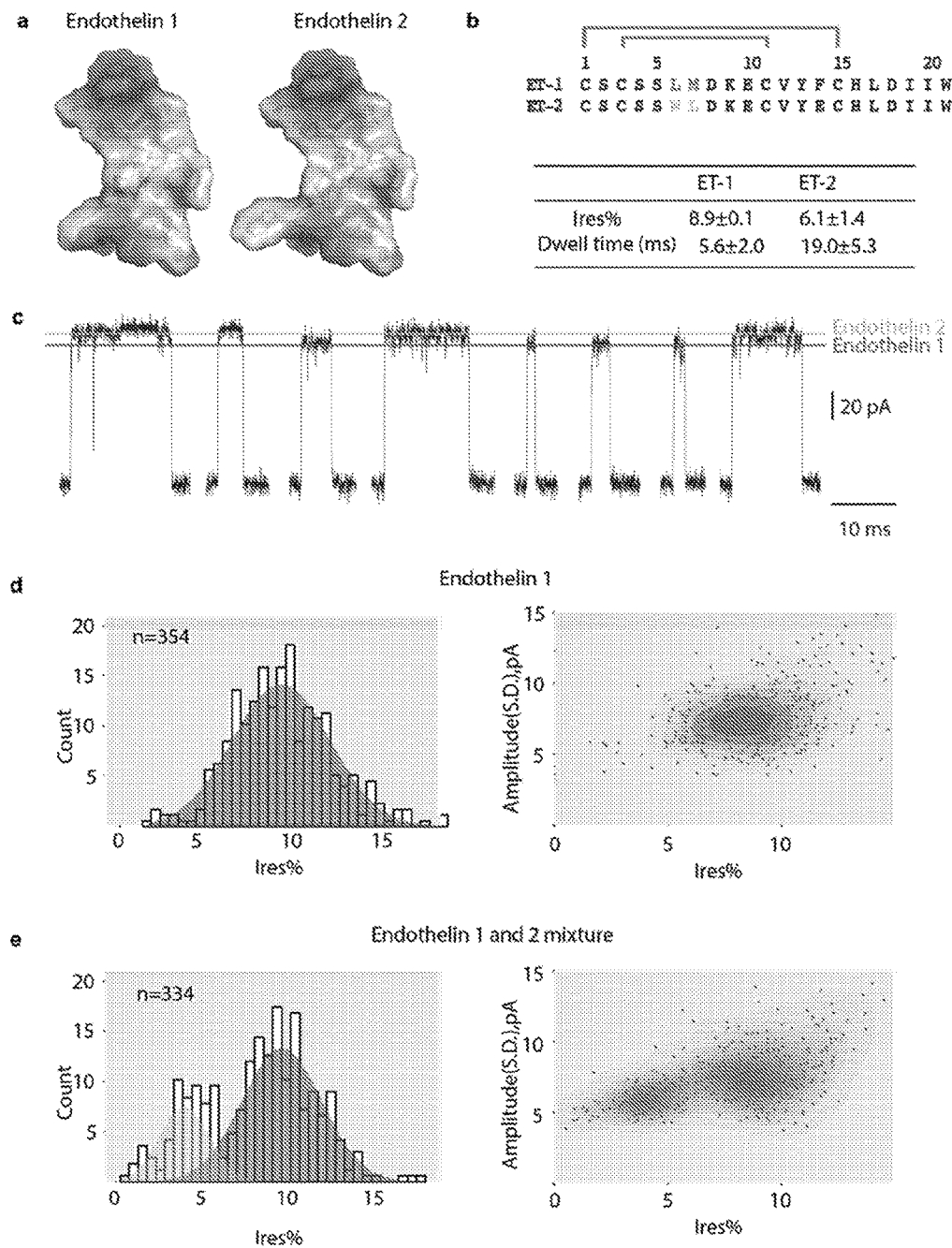

FIG. 13. Discrimination of endothelin 1 and 2 with WtFraC at pH 4.5. a) Molecular surface representation of endothelin 1 and endothelin 2 using electrostatic coloring (PyMOL). b) Above: amino acid sequences of endothelin 1 and 2. Blue lines indicate the disulfide bridges in each oligopeptide. Below: Ires % and dwell time for endothelin 1 and endothelin 2 blockades at –50 mV in pH 4.5 buffer (1 M KCl, 0.1 M citric acid, 180 mM Tris.Base). c) Representative endothelin 1 and endothelin 2 blockades to the same FraC nanopore under –50 mV applied potential. d) Histogram (left) of residual currents provoked by 2 µM endothelin 1 and corresponding heatplot depicting the standard deviation of the current amplitude versus Ires % (right). e) Same as in (d) but after addition of 8 µM endothelin 2 to the same pore revealing a second population. Graphs were created with custom R scripts. All recordings were conducted with 50 kHz sampling rate and 10 kHz Bessel low-pass filter.

EXPERIMENTAL SECTION

Section A

Materials and Methods

Unless otherwise specified, all chemicals were bought from Sigma-Aldrich. DNA was purchased from Integrated DNA Technologies (IDT). Enzymes were acquired from Fermentas and lipids from Avanti Polar Lipids. All errors in this work are given as standard deviations.

FraC Cloning

To allow cloning, a Nco I restriction site (CCATGG) was introduced at the beginning of the DNA sequence (5' end) corresponding to mature WtFraC from *A. fragacea*. To maintain the reading frame an additional two bases were inserted after the Nco I site, resulting in an additional alanine residue after the starting methionine. For purification purposes, at the C-terminus of FraC, a His9 affinity tag was attached via a flexible glycine-serine-alanine linker and the open reading frame was terminated by two consecutive stop codons, followed by a Hind III restriction site (3' end). 50 ng of the synthetic gene with optimized codon composition (IDT) served as a template for the following PCR reaction: the gene was amplified by Phire Hot Start II DNA polymerase (Finnzymes) using 6 μM of primers Frf and Frr (Table 2) in 300 μL volume. The PCR protocol was as follows: a pre-incubation step at 98° C. for 30 s was followed by 30 cycles of denaturation at 98° C. for 5 s and extension at 72° C. for 1 min. The resulting PCR product containing the Hi9-tagged WtFraC gene was purified with QIAquick PCR Purification Kit (Qiagen) and digested with Nco I and Hind III (FastDigest, Fermentas). The gel purified insert (QIAquick Gel Extraction Kit, Qiagen) was cloned under control of the T7 promoter into the pT7-SC1 expression plasmid using sticky-end ligation (T4 ligase, Fermentas) via Nco I (5') and Hind III (3') sites. Of the ligation mixture 0.6 μL was transformed into 50 μL of E. cloni® 10 G cells (Lucigen) by electroporation. The transformed bacteria were grown overnight at 37° C. on ampicillin (100 μg/ml) LB agar plates. The identity of the clones was confirmed by sequencing.

Construction of 10R FraC

Of the pT7-SC1 plasmid containing the WtFraC gene 100 ng served as a template for PCR reaction: the gene was amplified by Phire Hot Start II DNA polymerase (Finnzymes) using 6 μM of primers 10Rf (encoding for D10R) and T7 terminator (Table 2) in a 300 μL volume. The PCR reaction cycling protocol was as follows: a pre-incubation step at 98° C. for 30 s was followed by 30 cycles of denaturation at 98° C. for 5 s and extension at 72° C. for 1 min. The PCR product was gel purified (QIAquick Gel Extraction Kit, Qiagen) and cloned into a pT7 expression plasmid (pT7-SC1) by MEGAWHOP procedure[1]: about 500 ng of the purified PCR product was mixed with about 300 ng of the pT7-SC1 plasmid containing WtFraC gene and the amplification was carried out with Phire Hot Start II DNA polymerase (Finnzymes) in 50 μL final volume (pre-incubation at 98° C. for 30 s, then 30 cycles of: denaturation at 98° C. for 5 s, extension at 72° C. for 1.5 min). The circular template was eliminated by incubation with Dpn I (1 FDU) for 2 hr at 37° C. Of the resulting mixture 0.6 μL was transformed into E. cloni® 10 G cells (Lucigen) by electroporation. The transformed bacteria were grown overnight at 37° C. on ampicillin (100 μg/ml) containing LB agar plates. The identity of the clones was confirmed by sequencing.

Construction of 10R FraC Libraries by Error-Prone PCR

Libraries were constructed by amplifying the D10R FraC gene from plasmid DNA using T7 promoter and T7 terminator primers (Table 2).

TABLE 2

Oligonucleotides employed in this study. "5Biosg" stands for biotin group conjugated to 5' end of DNA via C6 linker (IDT).

| Name | DNA sequence |
| --- | --- |
| Frf | atatatatatccATGGCGAGCGCCGATGTCGCGGGTGCGG |
| Frr | atatatatatAAGCTTATCAGTGATGGTGGTGATGATGCGCAG |
| 10Rf | GCCGATGTCGCGGGTGCGGTAATCcgtGGTGCGGGTCTGGGCTTTGACGTAC |
| Oligonucleotide I | /5Biosg/AAAAAAAAAAAAAAAAAAAAGTGCTACGACTCTCTGTGTGCCCCCCCCCCCCCCCCCC |
| Oligonucleotide II | CACACAGAGAGTCGTAGCAC |
| $A_{20}$ | /5Biosg/ATATATAAAAAAAAAAAAAAAAAAAA |
| $C_{20}$ | /5Biosg/ATATATCCCCCCCCCCCCCCCCCCCC |
| $T_{20}$ | /5Biosg/ATATATTTTTTTTTTTTTTTTTTTTT |
| T7-terminator | GCTAGTTATTGCTCAGCGG |
| T7-promoter | TAATACGACTCACTATAGGG |

In the first round of mutagenesis we used a plasmid containing the synthetic gene encoding for 10R FraC as a template. In the second mutagenesis round we used the pool of DNA plasmids from the clones with highest activity identified in the first round of screening. DNA amplification was performed by error prone PCR: 400 μL of PCR mix (200 μl of REDTaq ReadyMix, 6 μM T7 promoter and T7 terminator primers, ~400 ng of plasmid template) was split into 8 reaction volumes containing from 0 to 0.2 mM of $MnCl_2$ and cycled for 27 times (pre-incubation at 95° C. for 3 min, then cycling: denaturation at 95° C. for 15 s, annealing at 55° C. for 15 s, extension at 72° C. for 3 min). These conditions typically yielded 1-4 mutations per gene in the final library. The PCR products were pooled together, gel purified (QIAquick Gel Extraction Kit, Qiagen) and cloned into a pT7 expression plasmid (pT7-SC1) by MEGAWHOP procedure: ~500 ng of the purified PCR product was mixed with ~300 ng of pT7-SC1 plasmid containing 10R FraC gene and the amplification was carried out with Phire Hot Start II DNA polymerase (Finnzymes) in 50 μL final volume (pre-incubation at 98° C. for 30 s followed by 30 cycles: denaturation at 98° C. for 5 s, extension at 72° C. for 1.5 min). The circular template was eliminated by incubation with Dpn I (1 FDU) for 2 hr at 37° C. Of the resulting mixture 0.6 μL was transformed into E. cloni® 10 G cells (Lucigen) by electroporation. The transformed bacteria were grown overnight at 37° C. on ampicillin (100 μg/ml) LB agar plates typically resulting in >10$^5$ colonies which were harvested for plasmid DNA library preparation.

Screening for Hemolytic Activity in Crude Lysates After FraC Overexpression

Overnight starter cultures from 600 clones (see above) were inoculated into 450 μL of fresh medium in new 96-deep-well plates and cultures were grown at 37° C. until OD600~0.8. Then, IPTG (0.5 mM) was added to induce overexpression and the temperature was reduced to 25° C. for an overnight incubation. Bacteria were harvested the following day by centrifugation at 3000×g for 15 min at 4° C. The supernatant was discarded and pellets were frozen at −80° C. for two hours to facilitate cell disruption. Cell pellets were then resuspended in 0.4 mL of lysis buffer (15 mM Tris.HCl pH 7.5, 1 mM MgCl2, 10 μg/ml lysozyme, 0.2 units/mL DNAse I) and lysed by shaking at 1300 RPM for 30 min at 37° C. Of the crude lysate 0.5-5 μL were then added to 100 μL of ~1% horse erythrocytes suspension. The latter was prepared by centrifuging horse blood (bioMerieux Benelux) at 6000×g for 5 min at 4° C. and pellet resuspension in 15 mM Tris.HCl pH 7.5, 150 mM NaCl. If the supernatant had a red color, the solution was centrifuged again and the pellet resuspended in the same buffer. The hemolytic activity was monitored by the decrease in OD at 650 nm over time (Multiskan GO Microplate Spectrophotometer, Thermo Scientific).

Screening for Mutations that Compensate for Deleterious Effects of D10R Amino Acid Substitution in FraC D10R amino acid substitution resulted in ~5 fold decrease in hemolytic activity of FraC (FIG. 5). Although D10R FraC still could be oligomerized and reconstituted in planar bilayers made from 1,2-diphytanoyl-sn-glycero-3-phosphocholine (DPhPC) we searched for compensatory mutations that recovered the hemolytic activity of D10R FraC back to the WtFraC level. Maintaining the hemolytic activity of FraC is important for two reasons: firstly, it reflects the ability to assemble into oligomeric pores on targeted lipid bilayers and, therefore, may translate into more efficient preparation of oligomeric nanopores. On the other hand, hemolytic activity offers a convenient way to screen the functionality of variants with arbitrary amino acid sequences changes and thus will facilitate future engineering efforts on the FraC nanopore. In order to identify compensatory mutations, we constructed a random mutagenesis library based on D10R FraC gene, transformed it into Bl21 DE3 *E. coli* and screened individual variants for hemolytic activity against horse erythrocytes in crude lysates after overexpression, using WtFraC as reference. In the first round, we screened 600 variants and selected 12 clones as a template for second round of random mutagenesis combined with hemolytic activity screening. Then, 7 clones with the highest level of hemolytic activity were selected for further characterization. Sequence changes that occurred in the corresponding genes are summarized in Table 3.

TABLE 3

Sequence changes that compensate for deleterious effects of D10R mutation in FraC.

| FraC variant | Amino acid sequence changes relative to WtFraC (residue numbering as in crystal structure PDB ID 4TSY) |
|---|---|
| 1 | D10R, T150I, W112L |
| 2 | I9T, D10R |
| 3 | A2S, D10R, G153D |
| 4 | D10R, A34V, A159E |
| ReFraC | D10R, K159E |
| 5 | D10R, I171T |
| 6 | I9T, D10R, F52Y, K159E |

Purified variants were oligomerized in sphingomyelin: DPhPC (1:1) liposomes and solubilized in 0.6% LDAO. After exchanging the detergent to 0.02% DDM by Ni-NTA chromatography, oligomeric proteins were tested for pore-forming activity in planar lipid bilayers composed of DPhPC. Initially, we identified variants named 3, 4 and ReFraC (Table 3) as the most promising pore-formers. However, nanopores made by variant 3 were heterogeneous (less than 50% yielded octameric pores), while pore-forming activity of variant 4 was decaying within days when stored at 4° C. Oligomeric ReFraC has maintained pore-forming activity for months when stored at 4° C. and formed nanopores nearly as uniform as a WtFraC while being able to capture ssDNA. Therefore, we picked ReFraC for further DNA analysis in this study. Further, we replaced aspartate 10 with asparagine in ReFraC yielding a D10N K159E variant, but could not detect ssDNA entry.

```
WtFraC (protein sequence)
MASADVAGAVIDGAGLGFDVLKTVLEALGNVKRKIAVGIDNESGKTWTA

MNTYFRSGTSDIVLPHKVAHGKALLYNGQKNRGPVATGVVGVIAYSMS

DGNTLAVLFSVPYDYNWYSNWWNVRVYKGQKRADQRMYEELYYHRSP

FRGDNGWHSRGLGYGLKSRGFMNSSGHAILEIHVTKAGSAHHHHHH**

WtFraC (DNA sequence)
ATGGCGAGCGCCGATGTCGCGGGTGCGGTAATCGACGGTGCGGGTCTG

GGCTTTGACGTACTGAAAACCGTGCTGGAGGCCCTGGGCAACGTTAAA

CGCAAAATTGCGGTAGGGATTGATAACGAATCGGGCAAGACCTGGACA

GCGATGAATACCTATTTCCGTTCTGGTACGAGTGATATTGTGCTCCCAC

ATAAGGTGGCGCATGGTAAGGCGCTGCTGTATAACGGTCAAAAAAATC

GCGGTCCTGTCGCGACCGGCGTAGTGGGTGTGATTGCCTATAGTATGT

CTGATGGGAACACACTGGCGGTACTGTTCTCCGTGCCGTACGATTATAA

TTGGTATAGCAATTGGTGGAACGTGCGTGTCTACAAAGGCCAGAAGCG

TGCCGATCAGCGCATGTACGAGGAGCTGTACTATCATCGCTCGCCGTTT

CGCGGCGACAACGGTTGGCATTCCCGGGGCTTAGGTTATGGACTCAAA

AGTCGCGGCTTTATGAATAGTTCGGGCCACGCAATCCTGGAGATTCAC

GTTACCAAAGCAGGCTCTGCGCATCATCACCACCATCACTGATAAGCTT
```

FraC Overexpression and Purification

E. cloni® EXPRESS BL21 (DE3) cells were transformed with the pT7-SC1 plasmid containing the FraC gene. Transformants were selected after overnight growth at 37° C. on LB agar plates supplemented with 100 mg/L ampicillin. The resulting colonies were inoculated into 2× YT medium (Sigma) containing 100 mg/L of ampicillin. The culture was grown at 37° C., with shaking at 200 rpm, until it reached an $OD_{600}$ of ~0.8. The expression of FraC was then induced by the addition of 0.5 mM IPTG and the growth was continued at 25° C. The next day the bacteria were harvested by centrifugation at 6000×g for 25 min and pellets were stored at −80° C. The pellets (derived from 50-100 ml of bacterial culture) containing monomeric FraC were thawed and resuspended in 40 ml of 15 mM Tris.HCl pH 7.5, 1 mM MgCl2 and 0.05 units/mL of DNase I (Fermentas). Then, to initiate cell disruption, bacteria suspension was supplemented with 0.2 mg/ml lysozyme and 2 M urea (to prevent debris formation) and was subjected to vigorous shaking at ambient temperature for 40 min. The remaining bacteria were disrupted by probe sonication. The crude lysates were clarified by centrifugation at 6000×g for 20 min and supernatant mixed with 200 µL (bead volume) of Ni-NTA resin (Qiagen) that was pre-equilibrated with wash buffer (10 mM Imidazole 150 mM NaCl, 15 mM Tris.HCl pH 7.5). After 1 hour of gentle mixing at ambient temperature, the resin was loaded onto a column (Micro Bio Spin, Bio-Rad) and washed with ~5 ml of wash buffer. FraC was eluted with approximately ~0.5 mL of wash buffer containing 300 mM imidazole. Protein concentration was determined by the Bradford assay. FraC monomers were stored at 4° C. until further use.

Hemolytic Activity Assay

Defibrinated horse blood (bioMerieux Benelux) was washed with 150 mM NaCl, 15 mM Tris.HCl pH 7.5 until the supernatant was clear. The erythrocytes were then resuspended with the same buffer to ~1% concentration (OD 650 nm 0.6-0.8). The suspension was then mixed with 200 nM of FraC. Hemolytic activity was measured by monitoring the decrease in OD650 using a Multiskan™ GO Microplate spectrophotometer (Thermoscientific). The rate of hemolysis was determined as one over the time elapsed till 50% decrease in turbidity.

Preparation of Sphingomyelin:DPhPC Liposomes 20 mg of the sphingomyelin (Brain, Porcine, Avanti Polar lipids) and DPhPC (1:1) mixture was dissolved in 4 ml of pentane supplemented with 0.5% ethanol (to help dissolving sphingomyelin) and placed in a round bottom flask. The solvent was evaporated while slowly rotating the flask in order to deposit lipid film on the walls. After deposition of the lipid film, the flask was kept open for 30 min to allow the complete evaporation of the solvent. The lipid film was then resuspended in 150 mM NaCl, 15 mM Tris.HCl pH 7.5 (final concentration of the total lipid 10 mg/ml) using a sonication bath (5-10 minutes at ambient temperature). Obtained liposomes were stored at −20° C.

Oligomerization of FraC

Monomeric FraC was mixed with liposomes (lipid/protein mass ratio 10:1) in 150 mM NaCl, 15 mM Tris.HCl pH 7.5 buffer. The mixture was briefly sonicated (sonication bath) and incubated for 30 min at 37° C. Proteoliposomes were then solubilized with 0.6% LDAO and incubated for 5 min and the mixture was diluted 20-fold with DDM-containing wash buffer (0.02% DDM 150 mM NaCl, 15 mM Tris.HCl pH 7.5) and mixed with ~100 µl (bead volume) of Ni-NTA agarose resin (Qiagen) that was pre-equilibrated with DDM-containing wash buffer. After gentle mixing for 1 hour, the resin was loaded onto a column (Micro Bio Spin, Bio-Rad) and washed with ~2 ml of DDM wash buffer. FraC was eluted from the column with 50 µl of elution buffer (200 mM EDTA, 0.02% DDM, pH 8—alternatively we could use 1M imidazole 0.02% DDM, however, EDTA proved more efficient). Purified FraC oligomers were stored at 4° C.

Alternatively, FraC oligomers can be formed by mixing FraC monomers with liposomes formed by sphingomyelin alone (1 hr at 37° C. and then 4° C. overnight). Next day, 5 mM EDTA and 1% DDM (final) is added to the proteoliposomes and incubated for 15 minutes at room temperature. The solution is then diluted to 1 ml volume containing 5 mM EDTA, 0.05% DDM 15 mM Tris HCl 7.5 150 mM NaCl. The solution is then concentrated to ~100 ul with 100 kDa cutoff ultrafiltration device.

Electrical Recordings in Planar Lipid Bilayers

The applied potential refers to the potential of the trans electrode. FraC nanopores were inserted into lipid bilayers from the cis compartment, which was connected to the ground electrode. The two compartments were separated by a 25 µm thick polytetrafluoroethylene film (Goodfellow Cambridge Limited) containing an orifice of ~100 µm in diameter. The aperture was pretreated with ~5 µl of 10% hexadecane in pentane and a bilayer was formed by the addition of ~10 µL of 1,2-diphytanoyl-sn-glycero -3-phosphocholine (DPhPC) in pentane (10 mg/mL) to both electrophysiology chambers. Typically, the addition of 0.01-10 ng of oligomeric FraC to the cis compartment (0.5 mL) was sufficient to obtain a single channel. WtFraC nanopores displayed a higher open pore current at positive than at negative applied potentials, which provided a useful tool to determine the orientation of the pore. Electrical recordings were carried out in 1M (initial characterization of the FraC nanopores) and in 3M NaCl (for polynucleotide analysis to increase amplitudes), 15 mM Tris.HCl pH 7.5.

Data Recording and Analysis

Electrical signals from planar bilayer recordings were amplified using an Axopatch 200B patch clamp amplifier (Axon Instruments) and digitized with a Digidata 1440 A/D converter (Axon Instruments). Data were recorded by using Clampex 10.4 software (Molecular Devices) and the subsequent analysis was carried out with Clampfit software (Molecular Devices). Electrical recordings were acquired by applying a 2 kHz low-pass Bessel filter and a 10 kHz sampling rate. Current transitions from level 0 to level 1 were analyzed with the "single-channel search" function in Clampfit. Residual current values ($I_{res}$) were calculated from blocked pore current values ($I_B$) and open pore current values ($I_O$) as $I_{res}=100*I_B/I_O$. $I_B$ and $I_O$ were determined from Gaussian fits to amplitude histograms of events. In case of events showing stepwise current enhancements, residual current levels were calculated from Gaussian fits to whole point current histograms. To determine event lifetimes, event dwell times ($t_{off}$) were binned together as cumulative distributions and fitted to a single exponential. Frequency of events that show stepwise current enhancements (FIG. 3A) and rotaxane forming blockades were calculated manually. Graphs were made with Origin (OriginLab Corporation) or Clampfit software (Molecular Devices).

Graphic Representation of FraC Nanopore

Molecular graphics was performed with Chimera (http://www.cgl.ucsf.edu/chimera).

EXAMPLE 1

Reconstitution of Wild Type FraC Pores in Planar Lipid Bilayers

Recombinant wild type FraC (WtFraC, FIG. 1A; 1B, top) protein monomers, genetically fused to a Hi9 tag at the C-terminus, were expressed in a BL21(DE3) *E. coli* strain. Previous works established that pore assembly of actinoporins is triggered by the presence of SM in lipid bilayers.[9], [10],[11],[8] In agreement, water-soluble monomers of WtFraC purified by Ni-NTA chromatography did not form pores in DPhPC planar lipid bilayers. Therefore, we pre-oligomerized monomers with DPhPC:SM (1:1) liposomes. After solubilization of the liposomes in 0.6% N,N-Dimethyldodecylamine N-oxide (LDAO), to prevent the dissociation of the oligomers,[12] LDAO was exchanged to 0.02% ß-Dodecyl maltoside (DDM) by a second round of Ni-NTA chromatography (SI). The addition of purified sub-microgram quantities of oligomeric WtFraC in 0.02% DDM to the cis side of the DPhPC planar lipid bilayer yielded pores readily. Distribution of unitary channel conductance for WtFraC pores at 1 M NaCl, 15 mM Tris.HCl pH 7.5 buffer revealed chiefly a single conductance type (FIGS. 1C; 4A, top), presumably corresponding to the octamer observed in the recently determined crystal structure.[8] Similar to other biological nanopores, WtFraC channels showed asymmetric current-voltage (I-V) relationship (FIG. 4B) allowing the determination of orientation of the pore. An example trace, obtained in 3 M NaCl, 15 mM Tris.HCl pH 7.5 buffer, is shown in FIG. 1D, top.

EXAMPLE 2

Engineering of WtFraC for Nucleic Acid Analysis

The crystal structure of octameric WtFraC suggests that this nanopore is large enough to allow the threading of ssDNA (1.2 nm constriction diameter).[8] However, in our initial experiments we could not observe ssDNA blockades, most likely because of the negatively charged constriction region of the WtFraC pore prevented DNA translocation. [13],[14] To induce the threading of ssDNA through FraC, we substituted aspartate 10 with arginine, producing a nanopore with a positively charged constriction (FIG. 1B, bottom). Because D10R FraC showed a low pore-forming activity (FIG. 5), we performed random mutagenesis on the background of the D10R FraC gene and screened hemolytic activity of obtained variants (SI). As a result, we identified the compensatory mutation lysine 159 to glutamic acid (K159E) which is located on the outer rim of the wide vestibule (FIG. 1A). The double mutant D10R, K159E of FraC (ReFraC) displayed near wild type-levels of hemolytic activity (FIG. 5) and yielded uniform pores (FIG. 1C), albeit with altered I-V relationship compared to WtFraC (FIG. 4B and FIG. 1D, bottom). The lower conductance of ReFraC pores at ±50 mV in 1 M NaCl, 15 mM Tris.HCl pH 7.5 can be attributed to a narrower constriction as arginine has bulkier side chain than aspartate (FIG. 1B).

EXAMPLE 3

Polynucleotide Discrimination with ReFraC

We followed established approaches with αHL[7],[15], [16],[17] and MspA[14],[18] to immobilize DNA with neutravidin (NA). We complexed 5'-end biotinylated A20/C20/T20 ssDNA homopolymers with tetrameric NA to assess the ability of ReFraC to translocate and discriminate DNA strands. We added pre-mixed DNA (1 µM) and NA (0.25 µM) to the cis compartment of the planar lipid bilayer setup and performed DNA discrimination experiments in 3 M NaCl, 15 mM Tris.HCl, pH 7.5 buffer and +70 mV applied potential (referring to the trans electrode). We observed permanent current blockades, which are provoked by pseudorotaxanes where ssDNA is stably threaded through the pore until the applied potential is reversed (FIGS. 2A, 9A). The residual currents, Ires, which are the percentage ratios of the amplitudes of blocked and open pore currents multiplied by 100 ((IMO)×100) were: 13.1±0.4% for NA:A20 (N=5, n=364, where N is a number of independent single pore experiments and n the analyzed blockades), 10.8±0.3% (N=4, n=920) for NA:C20 and 14.0±0.3%(N=5, n=780) for NA:T20 (FIG. 2B). To exclude effects of pore-to-pore variation, we also resolved mixtures of homopolymers (FIG. 2C-F). The relatively low residual currents suggest a tight closure of the pore around threaded ssDNA.

EXAMPLE 4

DNA Unzipping and Double Strand DNA Translocation by ReFraC Nanopores

The constriction of ReFraC (1.2 nm) is smaller than the B-form of double stranded DNA (dsDNA, ~2 nm). Thus, in order to evaluate dsDNA as a stopper for DNA analysis, we designed two oligonucleotides: oligo I with a biotin group attached at the 5'-terminus with the sequence bio-5'-A20-GTGCTACGACTCTCTGTGTG-C20-3' and a short oligo II with reverse complement sequence to the underlined part of oligo I. Annealing yielded an A(dsDNA)C substrate: a 20 base pair long central segment of dsDNA, flanked by A20 and C20 ssDNA segments. Addition of 1 µM of A(dsDNA)C to the cis compartment at +50 mV caused transient blockades to the ReFraC pore (blockade lifetime 2±5 s, Ires=10.0±0.2%, N=3, n=290, FIG. 6A, left). Increasing the applied potential to +70 mV shortened the blockades lifetime to 2.9±0.4 ms (note that the residual currents showed two current levels: 12.8±0.6% and 3.5±0.5% N=3 n=2700 FIG. 6B, left). The decrease of blockade lifetime with the potential suggests the translocation of A(dsDNA)C through ReFraC. To prove DNA translocation, we added NA to the cis chamber. NA:A(dsDNA)C blockades became permanent both at |+50 mV, (FIG. 6A, right) and at +70 mV (FIG. 6B, right), therefore suggesting the transient blockades in the absence of NA could not be provoked by the retraction of A(dsDNA)C to the cis compartment. Curiously, at +50 mV, 31±4% of the NA:A(dsDNA)C blockades (N=3, n=468) showed a stepwise enhancement of the residual current from a transient level (FIG. 3A, state "2", Ires=8.8±0.7%) to a stable level (FIG. 3A, state "3", with Ires=12.5±0.7%, N=4, n=46; more examples in FIG. 7). The current level of state "2" was slightly lower than that of NA:C20 (Ires=10.5±0.7; N=3, n=206 at +50 mV). The current level of state "3" matched that of NA:A20. A likely explanation for above current enhancements is that at +50 mV the C20 segment of NA:A(dsDNA)C is dwelling in the constriction of the nanopore (FIG. 3A, state "2"), with the duplex segment preventing the further translocation. However, after the unzipping of the duplex, A20 occupies the constriction of ReFraC, with NA arresting the translocation (FIG. 3A, state "3"). In agreement, at +50 mV, NA:A(dsDNA)C blockades were immediately relieved when the potential was reversed to −30 mV, indicating that at +50 mV translocation of A(dsDNA)C is mediated by unzipping (FIG. 3A, brackets).

In contrast, at +70 mV, a significant fraction of blockades was not immediately released at −30 mV (FIG. 3B, inset), indicating the formation of an interlocked state (FIG. 3B, states "2" and "3"). Further, these interlocked states were generated more frequently with increasing the potential (e.g. from 7±4% of all blockades at +70 mV to 54±14% at +100 mV, N=3, n=739; FIG. 3B, insert). Considering that blockades of oligo I alone in complex with NA were released immediately at −30 mV (FIG. 9A), we attribute such interlocked state to a rotaxane where NA and the duplex DNA segment of A(dsDNA)C serve as cis and trans stoppers, respectively (FIG. 3B, right). Expectedly, such rotaxanes could also be formed from NA:oligo I cis blockades by adding oligo II in trans (FIG. 9B). Switching potential to −40 mV dismantled rotaxanes quickly, presumably via unzipping of the dsDNA stopper in trans (FIGS. 8 and 9B). Formation of a rotaxane from NA:A(dsDNA)C present in cis requires the deformation of the ReFraC pore in order to allow the translocation of the duplex segment of the A(dsDNA)C substrate (FIG. 3B, brackets).

This structural flexibility may be a general feature of α-helical pores. Previously, we observed that the blockades of human thrombin (~4.2 nm diameter) to type I ClyA-CS nanopores (~3.3 nm constriction diameter) were followed by a transient increase in the open pore current.[19] This phenomenon was interpreted as translocation of the protein via the deformed constriction of ClyA.

REFERENCES TO SECTION A

[1] J. J. Kasianowicz, E. Brandin, D. Branton, D. W. Deamer, *Proc Natl Acad Sci USA* 1996, 93, 13770-13773.

[2] M. Akeson, D. Branton, J. J. Kasianowicz, E. Brandin, D. W. Deamer, *Biophys J* 1999, 77, 3227-3233.

[3] D. Wendell, P. Jing, J. Geng, V. Subramaniam, T. J. Lee, C. Montemagno, P. Guo, *Nature nanotechnology* 2009, 4, 765-772.

[4] L. Franceschini, M. Soskine, A. Biesemans, G. Maglia, *Nature communications* 2013, 4, 2415.

[5] C. Cao, Y. L. Ying, Z. L. Hu, D. F. Liao, H. Tian, Y. T. Long, *Nature nanotechnology* 2016.

[6] A. H. Laszlo, I. M. Derrington, B. C. Ross, H. Brinkerhoff, A. Adey, I. C. Nova, J. M. Craig, K. W. Langford, J. M. Samson, R. Daza, K. Doering, J. Shendure, J. H. Gundlach, *Nat Biotechnol* 2014, 32, 829-833.

[7] D. Stoddart, A. J. Heron, E. Mikhailova, G. Maglia, H. Bayley, *Proc Natl Acad Sci USA* 2009, 106, 7702-7707.

[8] K. Tanaka, J. M. Caaveiro, K. Morante, J. M. Gonzalez-Manas, K. Tsumoto, *Nature communications* 2015, 6, 6337.

[9] A. Barlic, I. Gutierrez-Aguirre, J. M. Caaveiro, A. Cruz, M. B. Ruiz-Arguello, J. Perez-Gil, J. M. Gonzalez-Manas, *J Biol Chem* 2004, 279, 34209-34216.

[10] B. Bakrac, I. Gutierrez-Aguirre, Z. Podlesek, A. F. Sonnen, R. J. Gilbert, P. Macek, J. H. Lakey, G. Anderluh, *J Biol Chem* 2008, 283, 18665-18677.

[11] P. Schon, A. J. Garcia-Saez, P. Malovrh, K. Bacia, G. Anderluh, P. Schwille, *Biophys J* 2008, 95, 691-698.

[12] K. Tanaka, J. M. Caaveiro, K. Tsumoto, *Biochemistry* 2015, 54, 6863-6866.

[13] G. Maglia, M. R. Restrepo, E. Mikhailova, H. Bayley, *Proc Natl Acad Sci USA* 2008, 105, 19720-19725.

[14] T. Z. Butler, M. Pavlenok, I. M. Derrington, M. Niederweis, J. H. Gundlach, *Proc Natl Acad Sci USA* 2008, 105, 20647-20652.

[15] R. F. Purnell, J. J. Schmidt, *ACS Nano* 2009, 3, 2533-2538.

[16] D. Stoddart, A. J. Heron, J. Klingelhoefer, E. Mikhailova, G. Maglia, H. Bayley, *Nano Lett* 2010, 10, 3633-3637.

[17] D. Stoddart, G. Maglia, E. Mikhailova, A. J. Heron, H. Bayley, *Angew Chem Int Ed Engl* 2010, 49, 556-559.

[18] E. A. Manrao, I. M. Derrington, M. Pavlenok, M. Niederweis, J. H. Gundlach, *PLoS One* 2011, 6, e25723.

[19] M. Soskine, A. Biesemans, M. De Maeyer, G. Maglia, *J Am Chem Soc* 2013, 135, 13456-13463.

[20] J. Mathe, H. Visram, V. Viasnoff, Y. Rabin, A. Meller, *Biophys J* 2004, 87, 3205-3212.

[21] N. An, A. M. Fleming, E. G. Middleton, C. J. Burrows, *Proc Natl Acad Sci USA* 2014, 111, 14325-14331.

[22] M. Faller, M. Niederweis, G. E. Schulz, *Science* 2004, 303, 1189-1192.

Section B

Section A herein above shows that an α-helical pore-forming toxin from an actinoporin protein family Fragaceatoxin C (FraC) is advantageously used for polynucleotide analysis.

Section B demonstrates that FraC nanopores are also suitable to recognize proteins, e.g. biomarkers, in the form of oligopeptides (~10 or fewer amino acids), polypeptides (>10 amino acids) and folded proteins (>50 amino acids).

Materials

Chymotrypsin(from bovine pancreas, ≥85%, C4129), ß2-microglobulin (from human urine, ≥98%, M4890), endothelin 1(≥97%, E7764), endothelin 2(≥97%,E9012), angiotensinI(≥90%, A9650), pentane(≥99%, 236705) and hexadecane(99%, 116703), Trizma® hydrochloride (Lot #SLBG8541V) and Trizma® base(Lot #SLBK4455V), N,N-Dimethyldodecylamine N-oxide (LADO, ≥99%, 40234) and n-Dodecyl ß-D-maltoside (DDM, ≥98%, D4641) were obtained from Sigma-Aldrich. Human EGF (≥98%, CYT-217) was obtained from PROSPEC. 1,2-diphytanoyl-sn-glycero-3-phosphocholine(DPhPC, 850356P) and sphingomyelin (Brain, Porcine, 860062) were purchased from Avanti Polar lipids. Potassium chloride (≥99%, Lot #BCBL9989V) was bought from Fluka. Citric acid(≥99%, Lot #A0365028) was obtained from ACROS. All polypeptide biomarkers and chemicals were used directly without further purification.

Note: 15 mM Tris, pH 7.5 buffer below used was prepared with the formula from Trizma® protocol: 1.902 g Trizma® HCl and 0.354 g Trizma® Base dissolved in 1 liter 1120 to be 15 mM Tris, pH 7.5.

Methods

FraC Monomer Expression and Purification

A gene encoding FraC with a C-terminal His6 tag was cloned into a pT7-SC1 expression plasmids using NcoI and HindIII restriction digestion sites. For expression, the plasmid was transferred into E.cloni® EXPRESS BL21(DE3) competent cell by electroporation. Transformants were harvested from the LB agar plate containing 100 mg/l ampicillin after overnight incubation at 37° C., and inoculated into 200 ml fresh liquid 2-YT media with 100 mg/l ampicillin. The cell culture was grown at 37° C., with 220 rpm shaking to an optical density at 600 nm of 0.8, then 0.5 mM IPTG was added to the cell culture. The temperature was lowered to 25° C. to induce the expression of FraC protein for 12 hours. Cells were recovered by 4,000 RPM centrifugation for 30 minutes at 4° C. and the cell pellets were kept at −80° C. 50-100 ml of cell culture pellet was thawed at room temperature, resuspended with 30 ml lysis buffer (15 mM Tris pH 7.5, 1 mM $MgCl_2$, 4 M Urea, 0.2 mg/ml lysozyme and 0.05 units/ml DNase) and mixed vigorously with a vertex shaker for 1 hour. In order to fully disrupt the cells, the suspension was sonicated for 2 minutes (duty cycle 10%, output control 3 of a Branson Sonifier 450). The crude lysate was then centrifuged at 6,500 RPM, 20 minutes at 4°

C. The supernatant (containing FraC monomers) was transferred to a 50 ml falcon tube containing a 100 µl of Ni-NTA resin (Qiagen, stored at 4° C., and suspended before pipetting out 100 µl), which was pre-washed with 3 ml of washing buffer (10 mM imidazole, 150 mM NaCl, 15 mM Tris, pH 7.5), and incubated at room temperature for 1 hour with gentle mixing. The resin was spun down at 4,000 RPM for 5 minutes at 4° C. Most of the supernatant was discarded and the pellet containing the Ni-NTA resin within ~5 ml of buffer was transferred to a Micro Bio Spin column (Bio-Rad) at RT. The Ni-NTA beads were washed with 10 ml wash buffer and the protein was eluted with 500 µl of 300 mM imidazole. Protein concentration was determined with NanoDrop 2000 (Thermo Scientific). The monomers were stored at 4° C.

Preparation of Sphingomyelin-DPhPC Liposomes 20 mg sphingomyelin (Brain, Porcine, Avanti Polar lipids) was mixed with 20 mg of 1,2-diphytanoyl-sn-glycero-3-phosphocholine (DPhPC, Avanti Polar lipids) and dissolved in 4 ml pentane (Sigma) containing 0.5% v/v ethanol. This lipid mixture was placed to a round flask and rotated slowly near a hair dryer to disperse the lipid well around the wall to evaporate the solvent. The flask was kept open at room temperature for another 30 minutes to let the solvent to evaporate completely. Then 4 ml of buffer (150 mM NaCl, 15 mM Tris, pH 7.5) was added to the dried lipids and the flask was added to a sonication bath for 5 minutes. Liposomes solution was kept at −20° C.

Oligomerization of FraC

Frozen liposomes were sonicated after thawing and mixed with monomeric FraC in a mass ratio 1:1. The FraC and liposome mixture was sonicated in a water bath for ~30 seconds and then kept at 37° C. for 30 minutes. The proteo-liposome was solubilized with 0.6% LADO(N,N-Dimethyldodecylamine N-oxide, 5% w/v stock solution in water), then transferred to a 50 ml falcon tube and diluted 20 times with buffer (150 mM NaCl, 15 mM Tris, pH 7.5, 0.02% DDM). 100 µl of pre-washed Ni-NTA resin (Qiagen) was added to the diluted protein/liposome mixture. After incubation with gentle shaking for 1 hour, the beads were loaded to column (Micro Bio Spin, Bio-Rad) and washed with 10 ml buffer (150 mM NaCl, 15 mM Tris, pH 7.5). FraC oligomers were eluted with 300 µl elution buffer (200 mM EDTA, 75 mM NaCl, 7.5 mM Tris, pH 8, 0.02% DDM). Oligomers can be stable for several weeks at 4° C.

Electrical Recording in Planar Lipid Bilayers

Electrical recordings were performed as described earlier[2]. In short, two chambers were separated by a 25 µm polytetrafluoroethylene film (Goodfellow Cambridge Limited) containing an aperture with diameter of around 100 µm. Two silver/silver-chloride electrodes were submerged into each compartment of the electrophysiology chamber, which was filled with 0.5 ml of buffer. The ground electrode was connected to the cis compartment, the working electrode to trans side. To form a lipid bilayer, ~5 µl of hexadecane solution (10% v/v hexadecane in pentane) was added to the polytetrafluoroethylene film. After ~2 minutes, 10 µl of a 10 mg/ml solution of 1,2-diphytanoyl-sn-glycero-3-phosphocholine (DPhPC) in pentane was added directly to the buffer in both compartments. A lipid bilayer then spontaneously formed by lowering the buffer above and below the aperture in the Teflon film. FraC oligomers were added to the cis side. Under an applied potential, the ionic current of FraC is asymmetric, which helps assessing the orientation of FraC nanopores in the lipid bilayer. FraC nanopores showed the orientation as shown in FIG. 10 when a higher conductance was measured at negative applied potential. Analytes were then added to cis chamber. Two kinds of buffer solutions were used for electrophysiology recording in this study depending on the pH. At pH 7.5 recordings were performed using 1M KCl and 15 mM Tris. When the pH was varied from 7.5 to 4.5, the buffer used contained 1 M KCl, 0.1 M citric acid, and 180 mM Tris.Base. FraC and ReFraC oligomers could insert into lipid bilayer from pH 4.5 to 7.5.

Data Recording and Analysis

Planar bilayer recordings were collected using a patch clamp amplifier (Axopatch 200B, Axon Instruments) and the data digitized with a Digidata 1440 A/D converter (Axon Instruments). Data were acquired by using Clampex 10.4 software (Molecular Devices) and the subsequent analysis was carried out with Clampfit software (Molecular Devices). Events duration (dwell time), time between two events (inter-event time), blocked current levels and open pore levels were detected by "single channel search" function. The current levels of blockades were referred as $I_B$, while the open pore current was referred as $I_o$. Ires %, defined as $(I_B/I_O)*100$, was used to describe the extent of blockade caused by different biomarkers. Average Inter-event times were calculated by binning the inter-event times and applying a single exponential fit to cumulative distributions.

Ion Selectivity Measurement

Ion permeability ratio ($K^+Cl^-$) was calculated using the Goldman-Hodgkin-Katz equation (Equation (1) herein below), which uses the reverse potential ($V_r$) as variable input. The $V_r$ was measured from extrapolation from I-V curves using asymmetric salt concentration condition as follow: Individual FraC nanopores were reconstituted using the same buffer in both chambers (symmetric conditions, 840 mM KCl, 15 mM Tris, pH 7.5, 500 µl) to assess the orientation of the nanopore. 400 µl solution containing 3.36 M KCl, 15 mM Tris, pH 7.5 was slowly added to cis chamber and 400 µl of a buffered solution containing no KCl (15 mM Tris, pH 7.5) was added to trans solution (trans:cis, 467 mM KCl: 1960 mM KCl). The solutions were mixed and I-V curves collected from −30 mV to 30 mV with 1 mV steps. Experiments at pH 4.5 were carried out using the same method but using 0.1 M citric acid buffered solutions. Initially, 500 µl buffer of 840 mM KCl, 0.1 M citric acid, 180 mM Tris.Base was added into both chamber and a single FraC channel obtained. Then, 400 µl of pH 4.5 solution containing 3.36 M KCl, 0.1 M citric acid, 180 mM Tris.Base was slowly added to cis chamber and 400 µl of a buffered solution containing no KCl (0.1 M citric acid, 180 mM Tris.Base, pH 4.5) was added to trans solution (thus yielding a trans:cis ration of 467 mM KCl: 1960 mM KCl). The solutions were mixed and I-V curves collected from −30 mV to 30 mV with 1 mV steps. The directionality of the ion selectivity was also tested by using high KCl concentration in trans chamber and low KCl concentration in the cis chamber. Ag/AgCl electrodes were surrounded with 2.5% agarose bridges containing 2.5 M NaCl.

EXAMPLE 5

Polypeptides and Protein Capture with FraC Nanopores

To assess FraC nanopores as a sensor for oligopeptides biomarkers, we initially selected endothelin 1, a 2.5 kD oligopeptide of 21 amino acids and α-II-chymotrypsin (henceforth chymotrypsin), a 25 kD globular protein of 245 amino acids (FIG. 10). Analytes were added to the cis side of wild type FraC (WtFraC) nanopores (FIG. 10A) using 1 M KCl, 15 mM Tris, pH 7.5 solutions and an external potential was applied to the "working" electrode located in the trans compartment. Because WtFraC shows gating above ~+50 mV, but is stable at potentials as high as −300 mV, we applied potentials between those limits. Addition of 1 μM of endothelin 1 to the cis compartment did not provoke blockades at ±50 mV (FIG. 10B) and up to −300 mV. Since the constriction of ClyA is lined with asp artic acid residues (FIG. 10A), we reasoned that the protonation of these residues at more acidic conditions should diminish the energy barrier for the translocation of endothelin 1 (carrying a net charge of −2) through the WtFraC constriction. Simultaneously, a less negative endothelin 1 would also migrate more easily towards the trans electrode under negative applied potentials. Endothelin 1 blockades started to be appear at pH 6.4, and their capture frequency increased linearly with decreasing the pH (from 0.6±0.2 events s$^{-1}$ μM$^{-1}$ at pH 6.4 to 10.8±2.3 events s$^{-1}$ μM$^{-1}$ at pH 4.4). At pH 4.5 (1 M KCl, 0.1 M citric acid, 180 mM Tris.Base), endothelin 1 blockades to WtFraC were observed at −50 mV (Ires %: 9.1±0.1%, dwell time: 5.6±2.0 ms, inter-event time: 5.8±0.7 ms), but not at +50 mV (FIG. 10B).

Encouraged by the effect of a more positive constriction under acidic conditions, we next investigated the capture of endothelin 1 with the D10R, K159E FraC (ReFraC) nanopore, a pore with arginine residues at the constriction engineered in Section A herein above for purposes of DNA analysis. Conversely to WtFraC, ReFraC is stable under positive applied potentials but displays gating at potentials of ~−50 mV. Thus, we only applied voltages between −50 mV to +200 mV to ReFraC. Addition of 1 μM endothelin 1 to the cis compartment elicited blockades at pH 7.5 at +50 mV (dwell time: 3.3±2.2 ms, inter-event time: 1413±223 ms) but not −50 mV (FIG. 10B). Decreasing to pH 4.5 (1 M KCl, 0.1 M citric acid, 180 mM Tris.Base) led to an increase in capture frequency at +50 mV (FIG. 10B, dwell time: 8.5±1.8 ms, inter-event time: 402±79 ms), despite the reduced electrophoretic mobility towards the trans electrode.

Next, the protein chymotrypsin (pI 8.75, Sigma) was tested as an example of a relatively large protein analyte. Protein blockades were observed at −50 mV in pH 7.5 buffer (1 M KCl, 15 mM Tris), although they became homogeneous when we increased the potential to −100 mV (45.2±19.1 events s$^{-1}$ μM$^{-1}$, dwell time: 12.0±5.7 ms), while no capture was observed at positive applied potentials (FIG. 10C). Contrary to what was observed with endothelin 1, the capture frequency of chymotrypsin remained constant between pH 7.5 and 5.5 (45.2±19.1 events s$^{-1}$ μM$^{-1}$ at pH 7.5, 50.5±22.6 events s$^{-1}$ μM$^{-1}$ at pH 6.4, 45.2±20.6 events s$^{-1}$ μM$^{-1}$ at pH 5.5,), and decreased when the pH was lowered to 4.4 (20.8±5.3 events s$^{-1}$ μM$^{-1}$ at pH 4.4). Using ReFraC at pH 7.5, we observed only few blockades at high positive applied potentials (dwell time: 0.2±0.1 ms, inter-event time: 174.3±22.9 ms at +200 mV) but not at −50 mV (FIG. 10C). Decreasing the pH to 4.5 led to an increase in capture frequency (dwell time: 1.3±0.7 ms, 112.5±9.5 events s$^{-1}$ μM$^{-1}$, FIG. 9B). Notably, ReFraC showed often shallow gating events at negative applied potentials under acidic conditions as shown in FIG. 10C bottom right. Taken together, both nanopores can capture analytes differing 10-fold in molecular weight (2.5 kD versus 25 kDa).

EXAMPLE 6

Ion Selectivity and Electrostatic Potential of FraC Nanopores

To gain a better insight into the influence of pH on the electrostatic environment and electro-osmotic flow on the entry of polypeptides inside FraC nanopores, we used the Adaptive Poission-Boltzmann Solver (APBS)(13) and a modified version of the PDB2PQR software(14) to estimate the electrostatic potential inside homology models of WtFraC and ReFraC at pH 7.5 and 4.5 in 1M KCl. The simulations showed that the constriction regions of WtFraC and ReFraC at the center of the nanopore exhibited highly negative and positive potentials, respectively (FIG. 11A). Interestingly, while for WtFraC the lowering of the pH from 7.5 to 4.5 caused a reduction potential at the center of the constriction from −1.2 to −0.7 kBT/e$_c$ (1 kBT/e$_c$=25.6 mV at 298 K) respectively, no such effect was observed for ReFraC.

The contribution of the electro-osmotic flow to the capture of analytes with WtFraC and ReFraC pores was estimated by measuring the ion-selectivity of both pores using asymmetric KCl concentrations on either side of the nanopore (1960 mM and 467 mM). The reversal potential (V$_r$), i.e. the potential at which the current is zero (FIG. 11B), was then used, together with the Goldman-Hodgkin-Katz equation, to calculate the ion selectivity (P$_{K^+}$/P$_{Cl^-}$) of both nanopores:

$$\frac{P_{K^+}}{P_{Cl^-}} = \frac{[a_{Cl^-}]_{trans} - [a_{Cl^-}]_{cis} \cdot e^{V_r F/RT}}{[a_{K^+}]_{trans} \cdot e^{V_r F/RT} - [a_{K^+}]_{cis}} \quad (1)$$

where [α$_x$]$_{comp}$ is the activity of ion X in the cis/trans compartments, R the gas constant, T the temperature and F the Faraday constant. We found that the ion selectivity of FraC nanopores is dominated by the charge at the constriction, with WtFrac being strongly cation-selective (P$_{K^+}$/P$_{Cl^-}$= 3.55±0.30, pH 7.5) and ReFraC anion-selective (P$_{K^+}$/P$_{Cl^-}$= 0.57±0.04, pH 7.5). Lowering of the pH to 4.5 decreased the cation-selectivity of WtFraC (P$_{K^+}$/P$_{Cl^-}$=2.02±0.15, pH 7.5) while it increased the anion-selectivity of ReFraC (P$_{K^+}$/P$_{Cl^-}$= 0.36±0.08, pH 4.5, FIG. 11B).

EXAMPLE 7

Biomarker Detection with the WtFraC Nanopore

After assessing the capture of chymotrypsin (25 kD, 245 amino acids) and endothelin 1 (12.5 kD, 21 amino acids), which are protein biomarkers for pancreatic cysts (15) and bronchiolitis obliterans (16), respectively, the WtFraC nanopores were used to detect a larger range of protein biomarkers including ß2-microglobulin, a 11.6 kDa (99 amino acids) biomarker for peripheral arterial disease (17), human EGF, a 6.2 kDa (53 amino acids) biomarker for chronic kidney disease (18), and angiotensin I, a 1.3 kD (10 amino acids) biomarker for hypertensive crisis (19).

All biomarkers were assessed under negative applied potentials and, with the exception of chymotrypsin, at pH 4.5. The capture frequency of all biomarkers increased with the applied potential. All other parameter tested showed a non-uniform voltage dependency. The residence time of the biomarkers inside WtFraC increased (chymotrypsin), decreased (ß2-microglobulin and angiotensin 1) or showed a bi-phasic behavior with the applied potential (EGF and endothelin 1) See FIG. 12. The voltage dependence of the residual current percentage (Ires %) of chymotrypsin decreased with the potential, the Ires % of endothelin 1 increased with the potential, while the Ires % of ß2-microglobulin, EGF and angiotensin 1 remained constant. Despite the complex voltage dependency of the current blockades, our results showed that the WtFraC nanopore is capable of distinguishing differently sized oligopeptide and protein biomarkers by virtue of the Ires % of their current blockades alone (FIG. 12).

EXAMPLE 8

Near-Isoform Oligopeptide Discrimination

In order to challenge our experimental system, we sought to identify highly similar analytes. We chose endothelin 1 (ET-1) and endothelin 2 (ET-2), near-isomeric oligopeptides differing in only one out of twenty-one amino acids (FIGS. 13A and 13B). At −50 mV, we observed distinguishable blockades with unique Ires % and dwell time (FIG. 12B) for ET-1 (Ires % 8.9±0.1%, dwell time 5.6±2.0 ms, N=3, n=600) and ET-2 (6.1±1.4%, dwell time 19.0±5.3 ms, N=3, n=384). This enabled already their identification on an individual blockade level (FIG. 13C).

Surprisingly, when we consecutively added first 2 µM ET-1 (FIG. 13D) followed by 8 µM ET-2 to the same pore (FIG. 13E), we could also separate a mixture of both two distinct populations by plotting the standard deviation of the amplitude of events over their corresponding Ires %. This observation indicates that highly similar (oligo)peptides or other analytes can be discriminated with a FraC nanopore.

The invention claimed is:

1. A method of detecting an analyte comprising
applying an electric field to a system comprising a funnel-shaped proteinaceous nanopore comprising an α-helical pore-forming toxin selected from the group consisting of Fragaceatoxin C (FraC), a mutant FraC, a FraC paralog, and a FraC homolog, wherein the funnel-shaped nanopore comprising the α-helical pore-forming toxin is positioned between a first conductive liquid medium and a second conductive liquid medium, wherein at least one of the conductive liquid media comprises an analyte, and wherein the analyte comprises an amino acid, a peptide, an unfolded peptide, an oligopeptide, an unfolded oligopeptide, a polypeptide, a protein, or an unfolded protein, and
detecting the analyte by measuring an ion current as the analyte interacts with the nanopore to provide a current pattern, wherein an appearance of a blockade in the current pattern indicates the presence of the analyte.

2. The method of claim 1, wherein the α-helical pore-forming toxin is FraC or a mutant FraC.

3. The method of claim 1, further comprising identifying the analyte.

4. The method of claim 3, wherein identifying the analyte comprises comparing the current pattern to a known current pattern obtained using a known analyte under the same conditions.

5. The method of claim 1, wherein the analyte is a protein having a size of from about 1 to about 40 kDa.

6. The method of claim 1, wherein the analyte is an oligopeptide (~10 or fewer amino acids), polypeptide (>10 amino acids) or folded protein (>50 amino acids).

7. The method of claim 1, wherein the system is operative to detect a property of the analyte by subjecting the nanopore to an electric field such that the analyte interacts with the nanopore.

8. The method of claim 1, wherein the system is operative to detect a property of the analyte by subjecting the nanopore to an electric field such that the analyte electrophoretically and/or electroosmotically translocates through the nanopore.

9. The method of claim 8, wherein the property is an electrical, chemical, or physical property of the analyte.

10. The method of claim 1, wherein the nanopore is comprised in a planar lipid bilayer.

11. The method of claim 10, wherein the lipid bilayer comprises or consists of phosphatidylcholine (PC), preferably 1,2-diphytanoyl-sn-glycero-3-phosphocholine.

12. The method of claim 1, wherein the system comprises FraC that is fused to a protein affinity tag comprising a His-tag or Strep-tag.

* * * * *